United States Patent [19]

Tsuji et al.

[11] Patent Number: 5,285,780
[45] Date of Patent: Feb. 15, 1994

[54] PACEMAKER WITH IMPROVED PULSE DETECTION

[75] Inventors: Takashi Tsuji, Fujisawa; Masayuki Horikawa, Yokohama, both of Japan

[73] Assignee: Nippon Zeon Co., Ltd., Tokyo, Japan

[21] Appl. No.: 797,889

[22] Filed: Nov. 26, 1991

[30] Foreign Application Priority Data

| Nov. 29, 1990 [JP] | Japan | 2-331881 |
| Nov. 29, 1990 [JP] | Japan | 2-331882 |
| Nov. 29, 1990 [JP] | Japan | 2-331883 |
| Nov. 29, 1990 [JP] | Japan | 2-331884 |

[51] Int. Cl.⁵ .............................................. A61N 1/362
[52] U.S. Cl. ............................................................. 607/13
[58] Field of Search ................................. 128/419 PG

[56] References Cited

U.S. PATENT DOCUMENTS

| 3,877,438 | 4/1975 | Cannon | 128/419 PG |
| 3,985,142 | 10/1976 | Wickham | 128/419 PG |
| 4,170,999 | 10/1979 | Allen et al. | 128/419 PG |
| 4,261,365 | 4/1981 | Nordling | 128/419 PG |
| 4,357,943 | 11/1982 | Thompson et al. | 128/419 PG |
| 4,543,956 | 10/1985 | Herscovici | 128/419 PG |
| 4,745,923 | 5/1988 | Winstrom | 128/419 PG |
| 4,821,724 | 4/1989 | Whigham et al. | 128/419 PG |
| 4,858,610 | 8/1989 | Callaghan et al. | 128/419 PG |

Primary Examiner—William E. Kamm
Assistant Examiner—Kennedy J. Schaetzle
Attorney, Agent, or Firm—Nikaido, Marmelstein, Murray & Oram

[57] ABSTRACT

Disclosed is a pacemaker having an output circuit which is set to a high impedance when the potential of the input signal transmitted through the input-output terminal is within a predetermined range, and is set to a low impedance when the potential of the signal is outside of the range. Therefore, the time when the input to an R wave detection circuit must be stopped due to the after potential becomes extremely short and the failure of detection of an R wave decreases and, further, there are no rapid fluctuations in the potential arising due to the on-off operation of the switch. Further, the pacemaker of the invention may include a pulse lowering circuit for inputting a lowering pulse to the R wave detecting circuit so that the pacing pulse and the following after potential can't be detected as the R wave of the electrical activity of the heart.

17 Claims, 23 Drawing Sheets

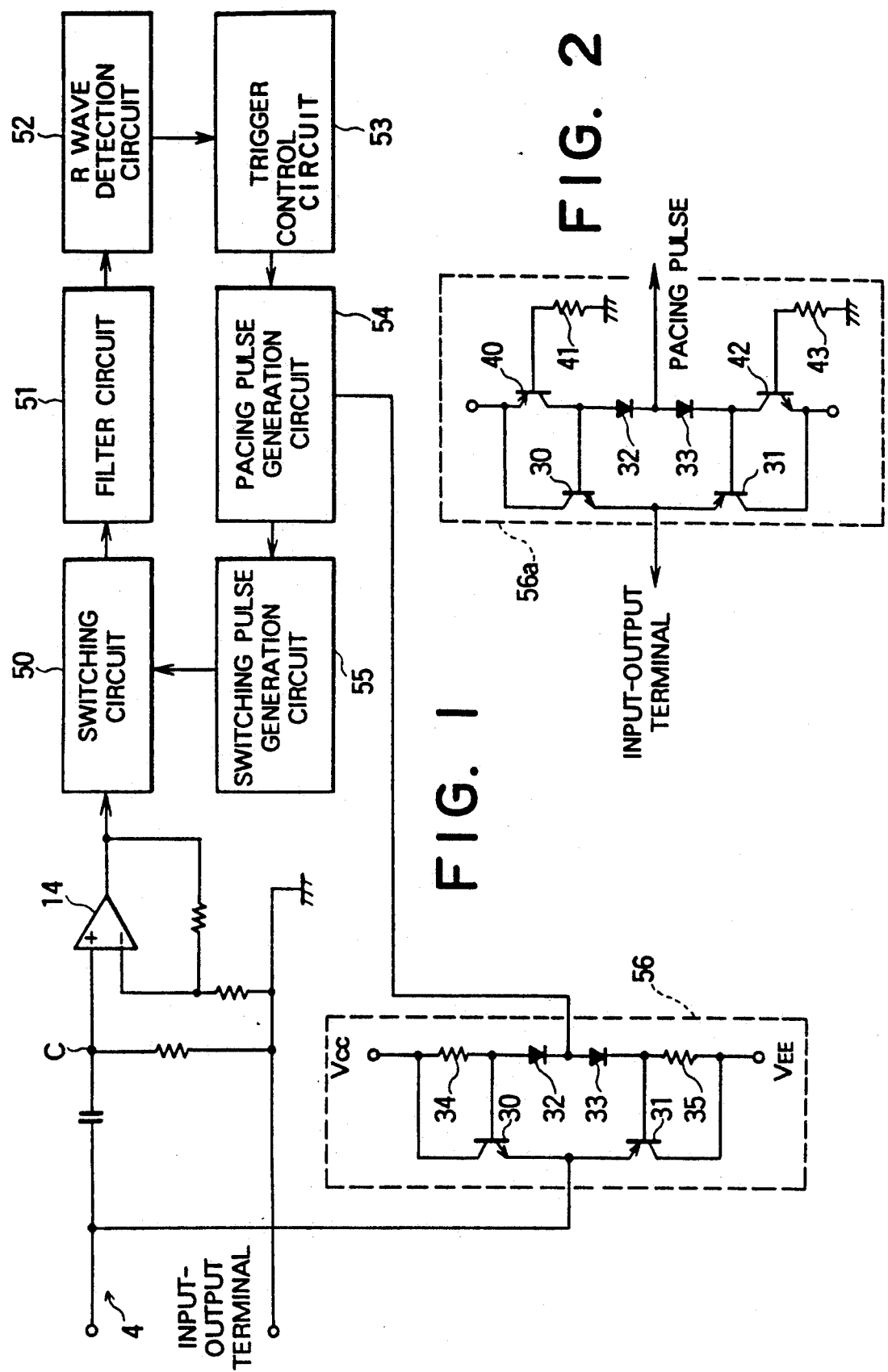

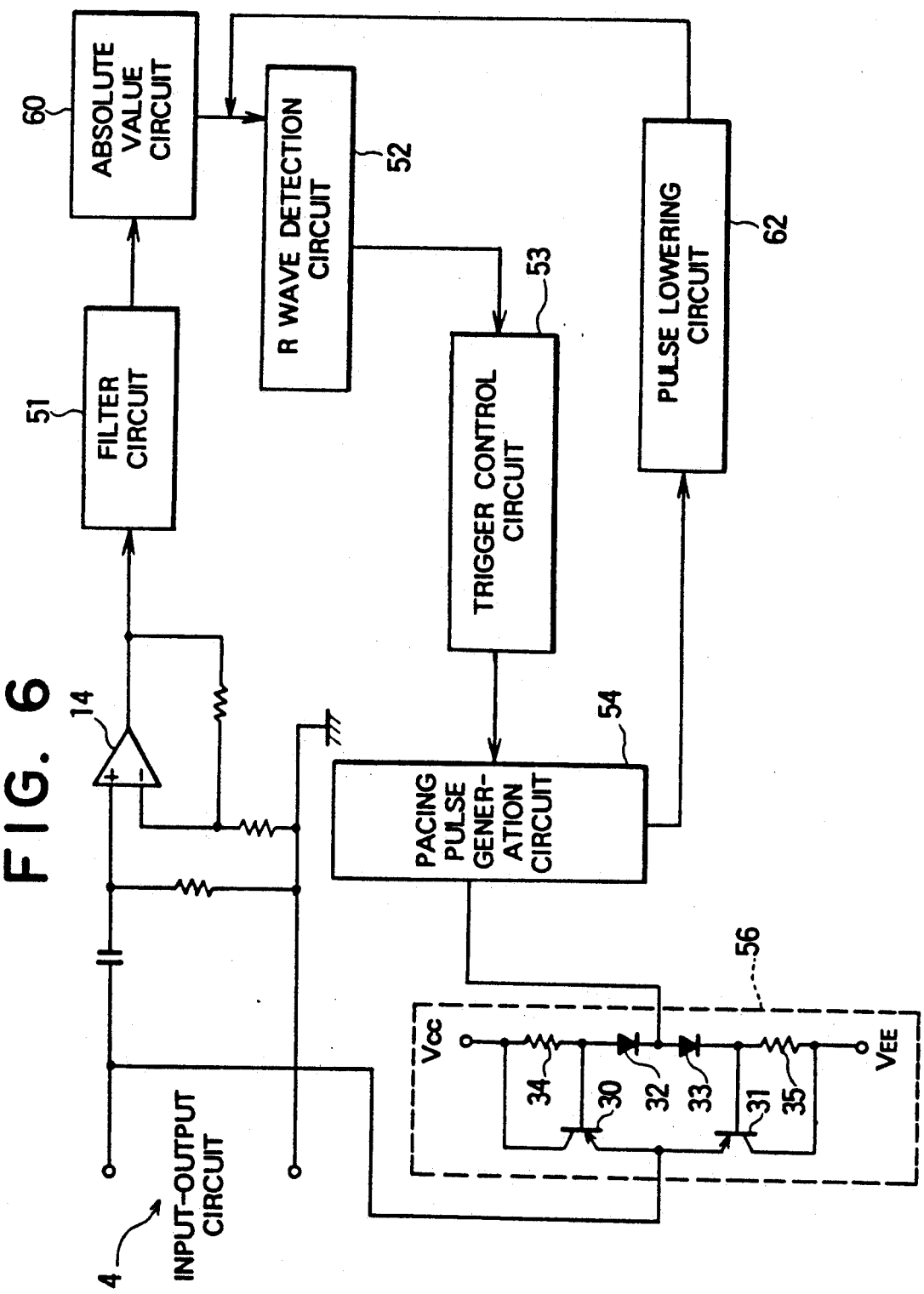

FIG. 7(A)
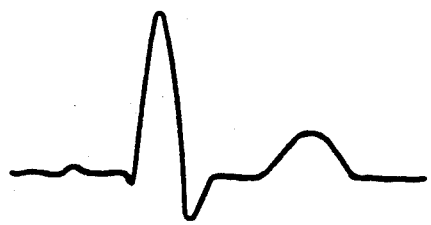
FIG. 7(B)
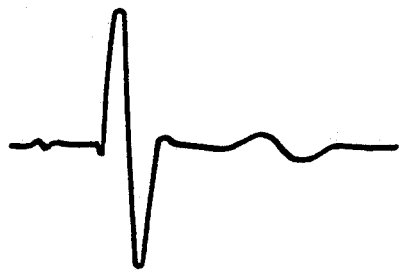
FIG. 7(C)
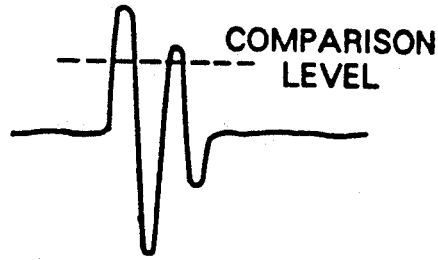
FIG. 7(D)
FIG. 8(A)
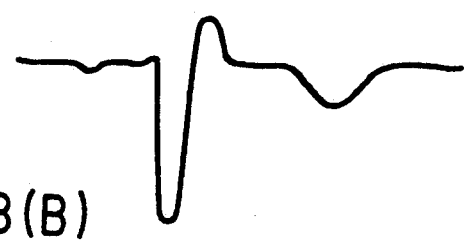
FIG. 8(B)
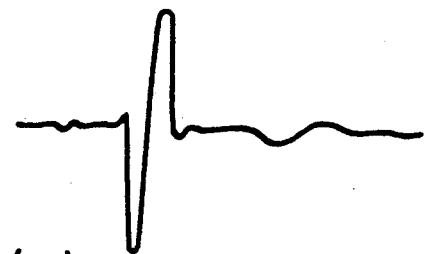
FIG. 8(C)
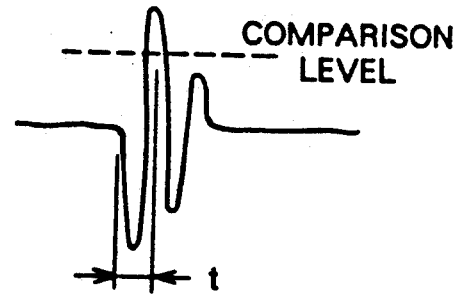
FIG. 8(D)

PACEMAKER WITH IMPROVED PULSE DETECTION

BACKGROUND OF THE INVENTION

1. Field of the Invention

The present invention relates to a pacemaker of the type which detects the electrical activity of the heart by electrodes disposed in the heart and outputs a pacing pulse from the electrodes, more particularly, relates to a pacemaker which is free from erroneous detection of a pacing signal and after potential etc. as an electrical activity of the heart.

2. Description of the Related Art

At the present time, for example, for patients suffering from acute cardiac infarction, patients after heart surgery, patients suffering from shock, etc., use is generally made of devices known as pacemakers when it is necessary to normalize the heart functions of the patients.

In such patients, use is made of external pacemakers when the need for normalization of the heart functions is transitional, while use is made of the implantation type pacemakers when it is perpetual.

For example, mounting an external pacemaker entails inserting and disposing a catheter with two electrodes in the right ventricle of the heart, then guiding lead wires from the pacing electrodes through the inside of the catheter to the outside of the body, and connecting the pacemaker body to the terminals of the same.

In such an external pacemaker, use is mainly made of a pacemaker of the type referred to as an external pacemaker of the type known as a demand type wherein pacing is performed when the heart beat of the body falls below a certain set number of beats and pacing is not performed with a number of heart beats above the set number of beats. Therefore, the electrical activity of the heart (wave height of 2 to 20 mV) caused between the two electrodes of the catheter inserted into the right ventricle is detected by the pacemaker and when the cycle interval between the R wave of the electrical activity and the next R wave is longer than the time corresponding to the set number of beats, a pacing pulse (wave height of 2 to 4 V and pulse width of 1 to 3 msec) is given between the two electrodes and passes through the cardiac muscle to cause contraction of the cardiac muscle. Therefore, during pacing, the heart is repeatedly made to beat forcibly at the set number of heart beats.

In this pacemaker, the input electrode and the output electrode are the same. Sometimes a weak voltage is received as input and sometimes a high voltage must be output by the same electrode.

Further, the input potential generated between the two electrodes in the right ventricle of the heart is due not only to the electrical activity of the heart. There are also fluctuations due to slow changes, that is, baseline fluctuations. Further, the large residual potential extending over a long period and caused after the pacing pulse is given, known as the after potential, that is, a residual potential as if a large capacitor had been connected in parallel between the electrodes, exists and this potential is input from the input-output terminal of the pacemaker. This residual potential is shown by the symbol A in FIG. 31, while a pseudo load circuit 2 constructed so as to enable pseudo reproduction of the residual potential is shown in FIG. 32. Note that the symbol B in FIG. 31 is a pacing pulse.

Therefore, in a circuit for detecting the electrical activity of the heart, unless the entry of the pacing pulse B and the after potential A into the detection circuit is prevented, these potentials will be detected and discrimination from the electrical activity of the heart will be impossible.

In a circuit for detecting the electrical activity of the heart, first the baseline fluctuation is eliminated using the input side as an AC coupling of a cutoff frequency of 10 to 30 Hz, then the signal is amplified several hundred fold by an amplifier, or the noise of the high band frequency is removed by passing the signal through a low pass filter, to obtain a signal stressing only the R wave of the electrical activity of the heart. This is detected by the comparison circuit when an R wave of more than a predetermined amplitude is input.

Usually, a detection circuit is given the function of detecting the electrical activity of the heart, then stopping the detection for 250 to 300 milliseconds. This is so as to prevent the detection off the S wave, T wave, or premature contraction etc. following the R wave of the electrical activity of the heart as shown in FIG. 33. Therefore, if the pacing pulse etc. is mistakenly detected, there is the inconvenience of the electrical activity of the heart not being able to be detected for the following 250 to 300 milliseconds.

Therefore, to avoid the effect of the pacing pulse and after potential, in the prior art, the following circuits are provided at the input-output terminal of the pacemaker.

First, a first circuit is the circuit shown in FIG. 34. In this circuit, provision is made of a switch 12 which completely separates the input and the output when the electrical activity of the heart is input and when a pacing pulse is output. When this switch 12 is set at the input side, that is, the solid line position of the figure, the electrical activity of the heart from the electrodes passes through the input-output terminal 4 and the switch 12 to reach the amplification circuit 14 where it is amplified and output to a detection circuit for detecting the R wave of the electrical activity of the heart. On the other hand, when outputting the pacing pulse, the switch 12 is set to the output side, that is, the dotted line position of the figure, for the time when the pacing pulse is output. If the input and the output are completely switched in this way, then it is possible to avoid the effects of the pacing pulse.

As such a circuit for performing the same operation as the first circuit, there is also the second circuit shown in FIG. 35. In this circuit, an output stage of the open collector or open drain connection is provided. In the same way as the first circuit, provision is made of a switch 15 which completely separates the input and output when the electrical activity of the heart is input and when the pacing pulse is output.

Further, as a third circuit, there is the circuit shown in FIG. 36. This circuit basically has the same construction as the circuit shown in FIG. 34. The switch 17 illustrated operates in the same way as the switch 12 of FIG. 34. The one different portion is that provision is made, in the input route from the switch 17 to the amplification circuit 14, of an RC filter having a cutoff characteristic of more than 1 Hz comprised of a capacitor 18 and a resistor 19. This filter is provided for eliminating the slowly changing fluctuations, that is, the baseline fluctuations. If the filter is not provided and the input terminal of the amplifier is directly connected to the input-output terminal, there is the danger of saturation of the amplifier due to the baseline fluctuation.

If provision is made of one of the above illustrated three circuits at the input-output terminal of the pacemaker, it is possible to avoid to a certain state the effects of the pacing pulse, but each of the circuits is designed to switch from the output side to the input side right after the output of the pacing pulse, so at the instant of the switching, the residual potential (after potential) is input and, for example, the amplification circuit ends up becoming saturated over a period of several hundred milliseconds and during that time it is impossible to detect the electrical activity of the heart.

To avoid this saturation, it is sufficient to prevent switching of the switch to the input side until the residual potential sufficiently attenuates, but with this the electrical activity of the heart detected by the pacing electrode cannot be input until the switching, so this does not basically resolve the problem.

Therefore, consideration has been given to a circuit which holds the input-output side at a low impedance for a short time after the pacing pulse is detected, forcibly discharges the R wave until a potential of a degree enabling detection of the electrical activity of the heart, then making the input-output side a high impedance and detecting the electrical activity of the heart.

Such a circuit is shown in FIG. 37 and FIG. 38. In the circuit shown in FIG. 37, provision is made of three switches: a switch 21 which connects a resistor 20, for discharging the after potential, to the input-output terminal 4, a switch 22 which turns on for the time when the pacing pulse is output, and a switch 23 for inputting the electrical activity of the heart from the input-output terminal 4 through a filter comprised of a capacitor 18 and a resistor 19 to the amplification circuit 14. The function of the filter and the function of the amplification circuit 14 are the same as in the above-mentioned circuit.

If the three switches are operated in the following way, then it is possible to cause saturation of the effect of the after potential. That is, at the time of the output of the pacing pulse, the switch 22 is turned on for about 2 milliseconds and a pulse with a relatively high potential is output to the input-output terminal. At this time, the switch 21 and the switch 23 are turned off. After the output of the pacing pulse, the switch 21 is turned on substantially simultaneously with the turning off of the switch 22 and the residual potential due to the after potential is forcibly attenuated through the resistor 20. This switch 21 is turned on until the residual potential attenuates to an extent not having an effect on the detection of the electrical activity of the heart (several tens of milliseconds).

Note that the switch 23 is turned off at this time too. The after potential sufficiently falls due to the operation of the switch 21, but does not fall completely to 0. Also, there is also baseline fluctuation. Therefore, the input-output terminal often does not become 0. This enables input of the electrical activity of the heart, but the slightly remaining after potential mentioned above is rapidly charged to the capacitor 18, so the amplification circuit 14 receives as input the pulse-like potential shown in FIG. 39(B). When the wave height of the pulse is large, it is not possible to differentiate it from the electrical activity of the heart and erroneous detection results.

To eliminate such trouble, in the circuit of FIG. 38, a switch 24 is connected in parallel with the resistor 19 at the connection point of the capacitor 18 and the resistor 19. This switch 24 is turned on for a period longer than a time constant determined by the capacitor 18 and the resistor 19 just before the switch 21 is turned off. If this is done, then it is possible to eliminate the trouble of receiving the pulse-like potential shown in FIG. 39(B). However, it is necessary to extremely precisely control the turning on and off of the four switches, so the control becomes complicated and therefore a large number of electronic circuits (electronic components) is needed, the device becomes larger, the reliability falls, and the current consumption increases, so there is the trouble of a shorter battery life.

SUMMARY OF THE INVENTION

An object of the present invention is to solve the problems accompanying the prior art as mentioned above and to provide a pacemaker which minimizes the detrimental effects of the after potential by an extremely simple and simply operating circuit and which is free from erroneous detection of the pacing pulse and after potential etc. as electrical activity of the heart.

The present invention, to achieve the abovementioned object, provides a first pacemaker comprising:

electrodes disposed in the heart for detecting the electrical activity of the heart;

an R wave detection circuit which detects an R wave of the electrical activity of the heart input from the electrodes and, when the R wave is detected, issues an output signal;

a pacing pulse generation circuit which discriminates a cycle of the R wave based on the output signal of the R wave detection circuit, is made not to output a pacing pulse when the R wave is detected at a cycle of less than a predetermined interval, and is made to output the pacing pulse from the electrodes when the R wave is not detected for more than a predetermined interval;

an input-output terminal which sends the input signal from the electrodes to the R wave detection circuit and sends the output signal from the pacing pulse generation circuit toward the electrodes;

an output circuit which is connected between the input-output terminal and the pacing pulse generation circuit, is set to a high impedance of at least more than 5 kiloohms when the potential of the input signal transmitted through the input-output terminal is within a predetermined range, and is set to a low impedance when the potential of the signal is outside of the range. The predetermined range is preferably narrower than the range of −600 mV to +600 mV.

According to the first pacemaker of the present invention, when just the electrical activity of the heart is input to the input-output terminal, since the electrical activity of the heart is in the range of ±20 mV, a range narrower than the range of −600 mV to +600 mV, the output circuit functions so that the input-output terminal is set to a high impedance. Therefore, the electrical activity of the heart, which has a signal source impedance of less than 1 kiloohm, will be input to the R wave detection circuit without attenuation. Further, just after the pacing pulse is output from the input-output terminal, the after potential is out of the range of −600 mV to +600 mV, so the output circuit functions so that the input-output terminal is set to a low impedance, therefore the after potential is rapidly attenuated to at least within the range of −600 mV to +600 mV and then gradually is attenuated in accordance with a time constant. Therefore, the time when the input to the R wave detection circuit must be stopped due to the after potential becomes extremely short and the failure of detection of the R wave decreases and, further, there are no rapid fluctuations in the potential arising due to the on-off operation of the switch.

Further, the present invention, to achieve the above-mentioned object, provides a second pacemaker comprising:

electrodes disposed in the heart for detecting the electrical activity of the heart;

an R wave detection circuit which detects an R wave of the electrical activity of the heart input from the electrodes and, when the R wave is detected, issues an output signal;

a pacing pulse generation circuit which discriminates a cycle of the R wave based on the output signal of the R wave detection circuit, is made not to output a pacing pulse when the R wave is detected at a cycle of less than a predetermined interval, and is made to output the pacing pulse from the electrodes when the R wave is not detected for more than a predetermined interval;

an input-output terminal which sends the input signal from the electrodes to the R wave detection circuit and sends the output signal from the pacing pulse generation circuit toward the electrodes;

an output circuit having a property of actively outputting a voltage until substantially 0 V or until the power source voltage, which is disposed between the pacing pulse generation circuit and the input-output terminal; and a pair of diodes connected in parallel and reverse to each other, which are disposed between the pacing output circuit and the input-output terminal.

According to the second pacemaker of the present invention, when just the electrical activity of the heart is input to the input-output terminal, since the electrical activity of the heart is in the range of ±20 mV, which is a relatively low range near 0 V, the output circuit and the reversely connected diodes function so that the input-output terminal is set to a high impedance. Therefore, the electrical activity of the heart will be input to the R wave detection circuit without attenuation. Further, just after the pacing pulse is output from the input-output terminal, the after potential is in an extremely high voltage range compared with the electrical activity of the heart, so the output circuit and the diodes function so that the input-output terminal is set to a low impedance. Therefore the after potential is rapidly attenuated to at least within the voltage range of the electrical activity of the heart near the forward direction voltage determined by the characteristics of the diodes and then gradually is attenuated in accordance with a time constant. Accordingly, the time when the input to the R wave detection circuit must be stopped due to the after potential becomes extremely short and the failure of detection of the R wave decreases. Further, there are no rapid fluctuations in the potential arising due to the on-off operation of the switches.

Further, the present invention, to achieve the above-mentioned object, provides a third pacemaker comprising:

electrodes disposed in the heart for detecting the electrical activity of the heart;

a comparison circuit, which generates an output signal when a signal of a predetermined value or more is input to detect an R wave of the electrical activity of the heart input from the electrodes;

a pacing pulse generation circuit which discriminates a cycle of the R wave based on the output signal of the comparison signal, is made not to output a pacing pulse when the R wave is detected at a cycle of less than a predetermined interval, and is made to output the pacing pulse from the electrodes when the R wave is not detected for more than a predetermined interval;

an absolute value circuit which is placed at the input side of the comparison circuit and makes the input signal entering the comparison circuit a signal of either a positive or negative unipolarity; and a pulse lowering circuit which, when the pacing signal in output from the electrodes, adds to the input signal of the unipolarity entering the comparison circuit from the absolute value circuit a lowering pulse of a polarity opposite to that polarity and of a potential larger than the input signal for a predetermined period.

Further, the present invention, to achieve the above-mentioned object, provides a fourth pacemaker comprising:

electrodes disposed in the heart for detecting the electrical activity of the heart;

a comparison circuit which generates an output signal when a signal of a predetermined value or more is input, to detect an R wave of the electrical activity of the heart input from the electrodes;

a pacing pulse generation circuit which discriminates a cycle of the R wave based on the output signal of the comparison signal, is made not to output a pacing pulse when the R wave is detected at a cycle of less than a predetermined interval, and is made to output the pacing pulse from the electrodes when the R wave is not detected for more than a predetermined interval; and a pulse lowering circuit which, when the pacing pulse is output from the electrodes, adds for a predetermined period to the input signal entering the comparison circuit a lowering pulse of a polarity opposite to the input signal and of a potential larger than the input signal.

According to the third and fourth pacemakers of the present invention, the lowering pulse is added to the input signal entering the comparison circuit for a predetermined period when a pacing signal is output from the electrodes. Therefor, the input signal is fully lowered by the lowering pulse to prevent erroneous detection of the pacing pulse and the following after potential as electrical activity of the heart in the comparison circuit. Accordingly, a switching circuit is not necessary to be provided to prevent erroneous detection of the pacing pulse as electrical activity of the heart. Further, even if a switching circuit is used, the pulse caused by the leakage current etc. of the same has no effect on the R wave detection of the comparison circuit.

BRIEF DESCRIPTION OF THE DRAWINGS

Other objects and features of the present invention will be described in detail with reference to accompanying drawings, in which FIGS. 1 and 6 are block diagrams of pacemakers according to a first aspect of the present invention;

FIGS. 2 and 3 are circuit diagrams showing modifications of the output circuit shown in FIG. 1;

FIGS. 7(A)-7(D), 8(A)-8(D) and 9(A)-9(C) are schematic views showing signal wave-forms in the middle of the circuits according to the present invention;

DESCRIPTION OF THE PREFERRED EMBODIMENTS

First Pacemaker

Figure 3:
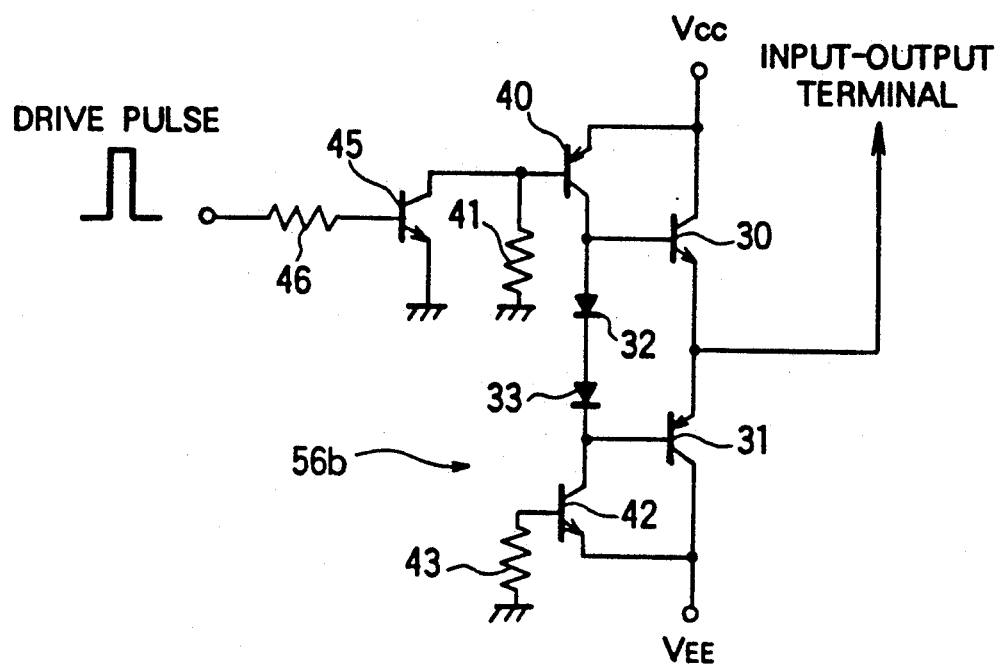

An explanation will now be made of a first pacemaker of the present invention with reference to the drawings.

The circuit construction of the first pacemaker according to the present invention shown in FIG. 1 is applied, for example, to an external pacemaker. The pacemaker may be applied to an internal pacemaker.

The input-output terminal 4 is, for example, connected to a pacing catheter having electrodes disposed in the ventricle through lead wires etc.

The electrical activity of the heart sampled by the pacing catheter disposed in the ventricle is an R wave of a wave height of 2 to 20 mV and has a polarity which sometimes is positive and sometimes is negative. This differs according to the position of the front electrode of the catheter and the position of the endocardium which it comes into contact with.

Therefore, the electrical activity of the heart detection circuit must detect two polarities. Usually, in an external pacemaker, to escape from the baseline fluctuation of the electrical activity of the heart, the input-output terminal 4 is made an AC coupling to cause attenuation of approximately 20 Hz or less, so that even an electrical activity of unipolarity is differentiated and becomes bipolar.

The input-output terminal 4 has connected to it an amplification circuit 14. In the amplification circuit 14, the weak electrical activity input from the input-output terminal 4 is amplified several hundred fold. The wave-form of the electrical activity input to the input-output terminal 4 is shown in FIGS. 7 and 8 (A). Further, the wave-form before the wave-form is differentiated and input to the amplification circuit 14 is shown in FIGS. 7 and 8 (B). The wave-form shown in FIG. 8 is reverse in polarity from the wave-form shown in FIG. 7, so as mentioned above, it is not known which wave-form enters the input-output terminal 4 according to the mounting position of the catheter etc.

The amplification circuit 14 has connected to it, in order, a switching circuit 50, a filter circuit 51, and an R wave detection circuit 52. The switching circuit 50 is a circuit which connects or cuts off the route to the R wave detection circuit 52 based on the output signal from a switching pulse generation circuit 55 when the electrical activity of the heart from the input-output terminal 4 is input and when the pacing pulse is output from the input-output terminal.

The filter circuit 51 is comprised of a low pass filter, high pass filter, etc. and is used to extract the R wave component. The R wave is applied directly to the R wave detection circuit 52. The output signal of the R wave from the filter circuit 51 has the wave-form as shown in FIGS. 7 and 8 (C).

The R wave detection circuit 52 may be any circuit which can detect an R wave, but for example is comprised of a comparison circuit. In an R wave detection circuit 52 comprised of a comparison circuit, for example, a slight threshold to the positive side is given. Therefore, when the R wave is not input, the level is below the comparison level, so the comparison circuit is not triggered, while when the R wave is input and the level exceeds the comparison level, the comparison circuit inverts and outputs a trigger pulse to a trigger control circuit 53. The wave-form of the R wave input to the R wave detection circuit 52 comprised of the comparison circuit is, as shown in FIGS. 7 and 8(C), inverted and changed in accordance with the state of the wave-form of the R wave input to the input-output terminal 4, but whatever the case if the R wave is input, then a positive polarity wave of more than the comparison level is input to the comparison circuit, so it is possible to detect the R wave. However, since a wave-form which inverts and changes in accordance with the state of the wave-form of the R wave input to the input-output terminal 4 is input to the comparison circuit, when an inverted wave-form such as shown in FIG. 8 is input to the comparison circuit, a detection time lag "t" occurs compared with the case where the wave-form shown in FIG. 7 is input. The detection time lag "t" is about 30 to 50 milliseconds, so is no problem.

The trigger control circuit 53 has the function of stopping the detection by the R wave detection circuit 52 for a predetermined time after the detection of the R wave of the electrical activity of the heart by an R wave detection circuit 52 comprised of a comparison circuit, and has the function of resetting the timer to make the pacing pulse output from the pacing generation circuit 54 mentioned later. The predetermined time after the R wave detection is a time sufficient for preventing detection of the S wave, T wave, or premature contraction after the R wave of the electrical activity of the heart shown in FIG. 33 and in general is 250 to 300 milliseconds. The trigger control circuit 53 is connected to the pacing pulse generation circuit 54, while the pacing pulse generation circuit 54 is connected through the output circuit 56 to the input-output terminal 4.

The pacing pulse generation circuit 54, in this embodiment, is a circuit which generates a pacing pulse in an adjustable predetermined time cycle. When an R wave is detected by an R wave detection circuit 52 comprised of a comparison circuit, the trigger control circuit 53 resets the timer calculating the predetermined time cycle and a pacing pulse is prevented from being output to the input-output terminal 4 for a predetermined time cycle from the input of the R wave. Further, when no R wave is detected by the R wave detection circuit 52 for a predetermined time from when one R wave is detected and the next R wave should be detected, a pacing pulse is output from the pacing pulse generation circuit 54 to the input-output terminal 4. When an R wave is not detected by the R wave detection circuit 52 for a predetermined time after the output of the pacing pulse, a pacing pulse is further output. This operation continues until an R wave is detected by the R wave detection circuit 52. The input-output terminal 4, as mentioned earlier, is connected to a catheter having electrodes implanted in the heart, so it is possible to pace the heart by the pacing pulse output from the input-output terminal 4.

The pacing pulse generation circuit 54 is connected to a switching pulse generation circuit 55 as well. The switching pulse generation circuit 55 is a circuit which generates a pulse for driving the switch in the switching circuit 50 in synchronization with the case where a pacing pulse is output from the pacing pulse generation circuit 54. That is, it has the function so that when a pacing pulse is output, it turns the switch in the switching circuit 50 off and cuts off the route to the R wave detection circuit 52 for a predetermined time, while when the pacing pulse is not output, turns the switch of the switching circuit 50 on and holds the route to the R wave detection circuit 52 in a connected state. Alternatively, the switching circuit may be one which short-circuits and cuts off the route to the R wave detection circuit 52.

In the present invention, due to the action of the output circuit 56 mentioned later, the after potential generated at the input-output terminal 4 after the pacing pulse is attenuated in a short time, so it is possible to set the circuit cutoff time by the switching circuit 50 to a short time. As the circuit cutoff time, specifically mention may be made of 50 to 150 milliseconds, preferably 50 to 80 milliseconds, after the output of the pacing pulse.

As the switching circuit 50, use may be made of the switching circuits such as shown in FIGS. 34 to 38 or other circuits. Note that such a switching circuit 50 may be at the input side of the amplification circuit 14.

In the present invention, provision is made of an output circuit 56 between the pacing pulse generation circuit 54 and the input-output terminal 4. This output circuit 56 is a circuit which is set to a high impedance of at least more than 5 kiloohms, preferably more than 10 kiloohms, when the potential of the signal transmitted through the input-output terminal 4 is a potential within a range narrower than the range of −600 mV to +600 mV, while is set to a low impedance when the potential of the signal is out of the above-mentioned range.

As a specific example of such a circuit, there is an emitter-follower complementary push-pull circuit such as shown in FIG. 1. In this circuits, the emitter terminals of the two transistors 30 and 31 are connected together, and the base terminals of the transistors 30 are connected by diodes 32, 33 connected in the forward direction toward the base of the one transistor 31. Further, between the bases and collectors of the transistors 30 and 31 is supplied a current to the diodes 32 and 33 connected with resistors 34 and 35 so that the diodes 32 and 33 are placed in the conductive state. The emitters of the two transistors 30 and 31 are connected to the input-output terminal 4, while the connection points of the diodes 32 and 33 are connected respectively to the pacing pulse generation circuit 54.

In this circuit, a bias current is given through the resistor 34 to the diode 32 having a forward direction falling voltage more than 20 mV, preferably 20 to 600 mV, lower than the conduction voltage between the base and emitter of the NPN transistor 30. This bias current is designed to be a current greater than the value of the current required for the output of the pacing pulse divided by the current amplification rate of the transistor 30. The same applies to the PNP transistor 31, the diode 33, and the resistor 35.

According to such an output circuit 56, in a range narrower than the range of −600 mV to +600 mV, preferably in the range of the electrical activity of the heart, that is, the range of −20 mV to +20 mV, the output impedance increases to more than 5 kiloohms, preferably more than 10 kiloohms, and in other ranges becomes extremely low. The range in which the output impedance becomes higher can be changed by selecting the forward direction voltage of the biasing diodes 32 and 33 connected in series or by selecting the type of the diodes. That is, as the diodes used, if use is made of usual silicon diodes with a low forward direction voltage drop, then a high impedance region can be obtained in the range of about ±70 mV (in range of about −70 to +70 mV).

The output circuit 56a shown in FIG. 2 has connected in it the constant current circuits comprised of the transistor 40 and the resistor 41 or the transistor 42 and the resistor 43 instead of the resistors 34 and 35 shown in FIG. 1. The constant current circuit comprised of the transistor 40 and the resistor 41 gives a positive bias current of the transistor 30, while the constant current circuit comprised of the transistor 42 and the resistor 43 gives the negative bias current of the transistor 31. In this circuit, the bias current is made a constant current, so it is possible to operate at a power source voltage lower than the power source voltages $V_{CC}$ and $V_{EE}$ shown in FIG. 1.

In these circuits, use is made of silicon Schottky barrier diodes, then a high region of output impedance can be obtained in the range of about ±0.25 V.

In the above two circuits, there is only a current amplification action and there is no voltage amplification function, so the voltage of the drive pulse to be given to the connection points of the diodes must be a voltage of equal to or greater than the output pulse voltage. Further, in the circuits, if a drive pulse voltage is given by a reverse polarity, it is possible to output an output pulse of the reverse polarity, that is, a pacing pulse.

The output circuit 56b shown in FIG. 3 is one which connects the voltage amplification stage comprised of the resistor 46 and the transistor 45 to the resistor 40 of the circuit shown in FIG. 2 and gives a drive pulse to the resistor 46. According to this circuit, there is the function of voltage amplification, so there is the merit that it is possible to freely select to a certain extent the voltage of the drive pulse. Further, by changing the emitter potential of the transistor 45, it is possible to change the potential of the voltage of the drive pulse. Also, if the transistor 45 is made a PNP transistor and the collector terminal is connected to the base of the transistor 42 to give the drive voltage by a reverse polarity, then it is possible to output a reverse polarity output pulse, that is, the pacing pulse. In this circuit, a high output impedance region can be obtained in the range of about ±100 mV.

In the circuits illustrated above, by selecting the forward direction voltage of the biasing diodes connected in series or by selecting zener diodes exhibiting suitable forward direction voltages, it is also possible to set the region where the output impedance rises to about ±20 mV.

In a usual electronic circuit, such circuits are not used since distortion is caused in the wave-form. That is, the common perception is that a bias higher than the conduction voltage across the bases and emitters of transistors is given, but in the present embodiments of the invention, the circuit is constructed so that the above-mentioned characteristic is realized. Further, consideration has been given to the use of a source-follower complementary push-pull circuit using field effect transistors instead of regular transistors, but field effect transistors suffer from large variations in the gate and source voltage, so are not industrially suitable, but if a relatively high precision field effect transistor is developed, it could be used in the present invention.

Figure 4:
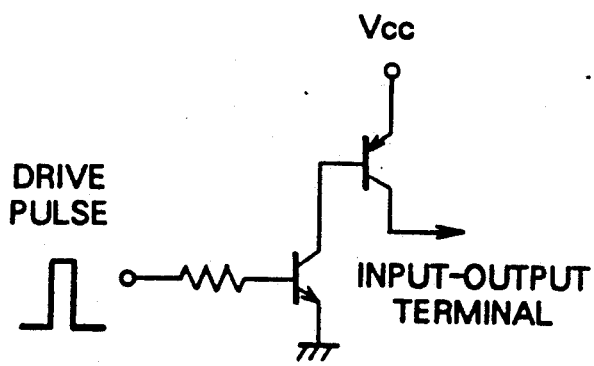
FIGS. 4 and 5 are circuit diagrams of output circuits according to comparative examples of the present invention.
Figure 5:
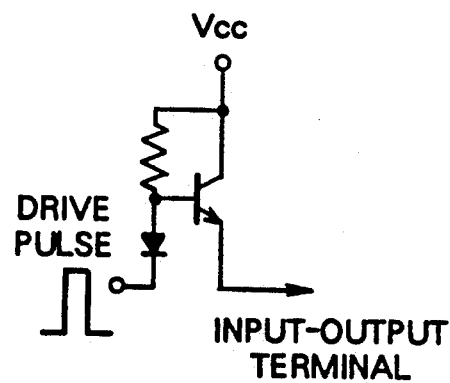

Note that the output circuit of the emitter ground shown in FIG. 4 cannot make a high impedance region near the 0 potential and that in the emitter-follower of a single transistor such as shown in FIG. 5, it is not possible to absorb an after potential of the same polarity as the output pulse.

According to the output circuits 56a and 56b of the present embodiment, it is possible to efficiently detect the R wave from the input-output terminal while the pacing pulse is not being generated and the after potential of the pacing pulse is rapidly attenuated when a pacing pulse is output from the input-output terminal, so the time when the input to the R wave detection circuit must be stopped due to the after potential becomes extremely short and the failure to detect R waves is reduced. Further, the output circuits do not use any switches, so there are no sharp fluctuations of the potential caused by turning switches on and off.

Note that the present invention is not limited to the above-mentioned embodiments and can be modified in various ways in the scope of the invention.

For example, the pacemaker according to the present invention is not limited in terms of the circuit constructions other than the output circuits 56, 56a, and 56b and for example may be of the circuit construction shown in FIG. 6.

In the circuit shown in FIG. 6, there is no need to provide the switching pulse generation circuit 55 and the switching circuit 50 shown in FIG. 1. Instead, provision may be made of an absolute value circuit 60 and a pulse lowering circuit 62.

In the absolute value circuit 60, the signal waveform which is input is converted into one of the positive and negative polarities. After this, the positive or negative polarity signal is applied to an R wave detection circuit 52 for detection of the R wave. For example, assume the output of the absolute value circuit 60 is positive and a positive wave is to be detected by the R wave detection circuit 52 comprised of a comparison circuit given a slight threshold in the positive polarity side. If so, then when the R wave is not input, the level is below the comparison level, so the R wave detection circuit 60 is not triggered, while when the R wave is input and the level exceeds the comparison level, the R wave detection circuit 52 comprised as a comparison circuit inverts and outputs a trigger pulse to the trigger control circuit 53. The output wave-form of the absolute value circuit 60 converted to a wave of the positive polarity is, for example, shown in FIGS. 7 and 8(D). As shown in these figures, if the absolute value circuit is passed through, even if a wave-form of the opposite polarity has been input to the input-output terminal 4, the output wave-form of the absolute value circuit 60 becomes the same wave-form.

The pulse lowering circuit 62 has the function so that when a pacing pulse is output toward the input-output terminal 4, it applies to the unipolarity input signal entering from the absolute value circuit 60 to the R wave detection circuit 52 a lowering pulse of a polarity opposite to that polarity and a potential larger than the input signal for a predetermined time so as to prevent the input of an input signal of larger than a predetermined value to the R wave detection circuit 52.

Figure 9A:
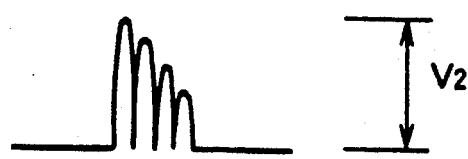
Figure 9B:
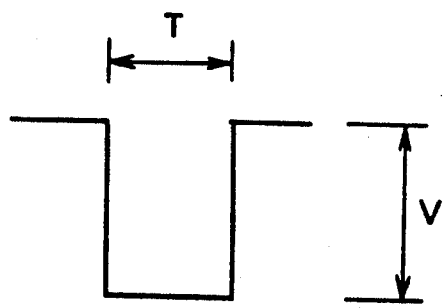
Figure 9C:
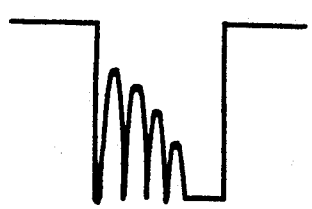

When the output signal from the absolute value circuit 60 is of a positive polarity, a negative polarity pulse, i.e., a polarity opposite to the positive one, shown in FIG. 9(B), is input to the input side of the R wave detection circuit 52. The width (time) T of the negative polarity pulse is preferably a width of more than the time of the effect of the pacing pulse input from the input-output terminal 4 and the after potential. The time T in general is 20 to 150 milliseconds. Further, the pulse voltage V is preferably larger than the maximum wave-form potential V2 of the pacing pulse and after potential shown in FIG. 9(A) passing through the amplification circuit 14, the filter circuit 51, and the absolute value circuit 60. At the input side of the R wave detection circuit 52, the pulse shown in (B) of the figure is applied to the wave-form shown in FIG. 9(A) corresponding to the pacing pulse and the after potential and becomes the wave-form shown in (C) of the figure.

Even if the wave-form shown in (C) of the figure is input to the R wave detection circuit 52, the wave-form corresponding to the pacing pulse and the after potential is sufficiently lowered by the lowering pulse, so the R wave detection circuit 52 comprised of a comparison circuit which detects signals of greater than the predetermined value will not erroneously detect a signal as an R wave. In the above explanation of the operation, the case was where the output of the absolute value circuit 60 was positive, but even if the circuit is constructed with the output of the absolute value circuit 60 is negative and the other succeeding polarities are all reversed, the circuit operates in the exactly same way.

If this construction is adopted, even if a switch element is not used, there is no longer any erroneous detection of the pacing pulse and the after potential by the R wave detection circuit 52 comprised of a comparison circuit as an R wave. Further, even if a switch element is used, the pulse due to the leakage current etc. does not have any effect on the detection of the R wave. The reason is that the switch operation is performed at the negative side opposite in polarity to the signal to be detected (no positive noise is produced).

In the circuit of the pacemaker too, if the output circuits 56, 56a, and 56b according to the first aspect of the present invention are connected between the pacing pulse generation circuit 54 and input-output terminal 4, the function is the same as the embodiment shown in FIG. 1. In particular, in this embodiment, even if a switching circuit is not used, there is no longer any erroneous detection of the pacing pulse and the after potential as an R wave by the R wave detection circuit 52 comprised of a comparison circuit and also the pulse lowering time T by the pulse lowering circuit 62 may be shortened, so this is convenient.

Figure 10:
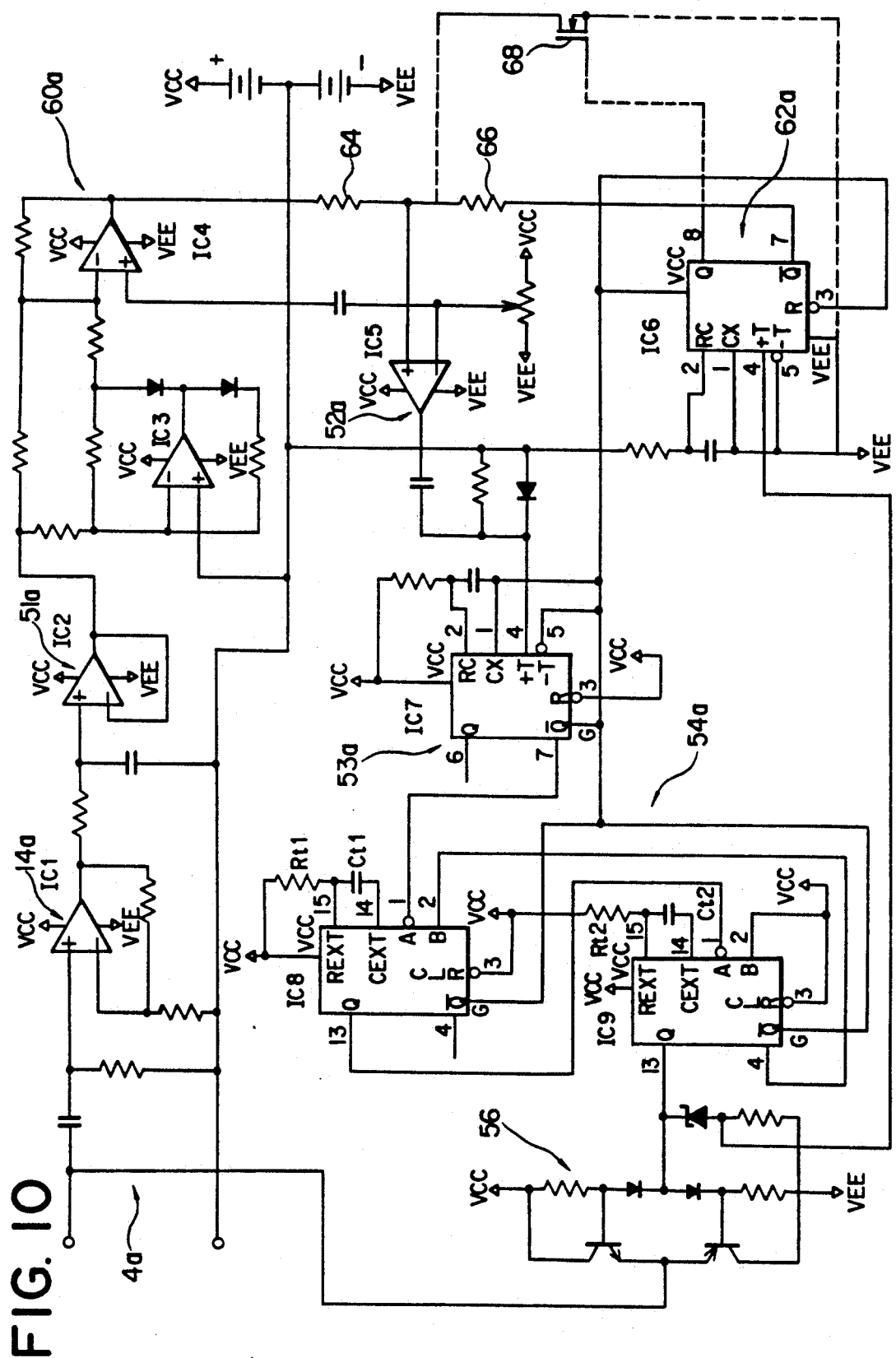
FIG. 10 is a circuit diagram in greater detail than the block diagram of FIG. 6.

A more detailed circuit diagram of the pacemaker 5 shown in FIG. 6 is shown in FIG. 10.

In FIG. 10, the reference 4a is an input-output terminal, and 14a is an amplification circuit which is comprised of an operational amplifier and has an amplification rate of several 100. Reference 51a is a filter, which is, for example, comprised of the low pass type and has a buffer of an operational amplifier. Reference 60a is an absolute value circuit, which is comprised of a typical circuit based on two operational amplifiers and outputs an output signal of a positive polarity. Reference 52a is a comparison circuit, which is comprised of an operational amplifier performing a comparator operation and is designed that the comparison potential is finely adjusted to the positive side. In the comparison circuit 52a, when a potential higher than the comparison potential is input, an output signal of a positive polarity is output, while at other times, a negative output signal is produced. The output from the absolute value circuit 60a is connected to the input end of the comparison circuit 52a through a resistor 64.

Reference numeral 62a is a switch signal generator, which operates with a negative power source. The switch signal generator is comprised of a one-shot multi-vibrator which shifts the level of the pacing output to make it a negative level and which enables, in synchronization with the rise of the pacing output, an output from 0 to the negative side from the output "$\overline{Q}$" and an output from the negative side to 0 from the output "Q". The one-shot multi-vibrator 62a is designed that the output starts to appear in synchronization with the rise of the pacing pulse and the output is stopped after tens to hundreds of milliseconds or so. The output side of the switch signal generator 62a is connected to the input side of the comparison circuit 52a through a resistor 66. The switch signal generator 62a and the resistor 66 comprise a pulse lowering circuit 62 as shown in FIG. 6. Instead of the resistor 66, use may be made of an FET 68. Further, instead of the resistor 66 or the FET 68, an open collector or an open drain transistor may be connected between the output of the signal generator 62a and the input end of the comparison circuit 52a, the emitter or the source of which may be connected to the negative power source and the base or gate of which may be switched by the negative potential.

Reference numeral 53a in FIG. 10 is a one-shot multi-vibrator which stops the detection for approximately 250 to 300 milliseconds after detection of the electrical activity of the heart. This multi-vibrator 53a has the function of receiving the output signal of the comparison circuit 52a, sending the reset signal to the pacing pulse generation circuit 54a, and resetting a timer for calculating the pulse interval of a next pacing pulse output from the pacing pulse generation circuit 54a. That is, the multi-vibrator 53a corresponds to the trigger control circuit shown in FIG. 6.

Note that the pacing pulse generation circuit 54 is designed to set the pulse interval and the pulse width by t1 and t2. Reference numeral 56 is a pacing pulse output circuit.

As clear from the above explanation, according to the first pacemaker of the present invention, when just the electrical activity of the heart is input to the input-output terminal, since the electrical activity of the heart is in the range of ±20 mV, a range narrower than the range of −600 mV to +600 mV, the output circuit functions so that the input-output terminal is set to a high impedance and the electrical activity of the heart will be input to the R wave detection circuit without attenuation. Further, when the pacing pulse is output from the input-output terminal, the after potential is out of the range of −600 mV to +600 mV, so the output circuit functions so that the input-output terminal is set to a low impedance. By this, the after potential is rapidly attenuated to at least within the range of −600 mV to +600 mV and then gradually is attenuated in accordance with a time constant. Therefore, the time when the input to the R wave detection circuit must be stopped due to the after potential becomes extremely short and the failure of detection of the R wave decreases. Further, there are no rapid fluctuations in the potential arising due to the on-off operation of the switch.

An explanation will now be made of the first pacemaker of the present invention using more detailed examples, however, the present invention is not limited to these examples.

A circuit as shown in FIG. 1 was prepared.

As the transistor 30, use was made of a 2SC2459, as the transistor 31, use was made of a 2SA1049, as the diodes 32 and 33, use was made of 1S953's, and as the resistors 34 and 35, use was made of ones of 200 kiloohms.

Figure 32:
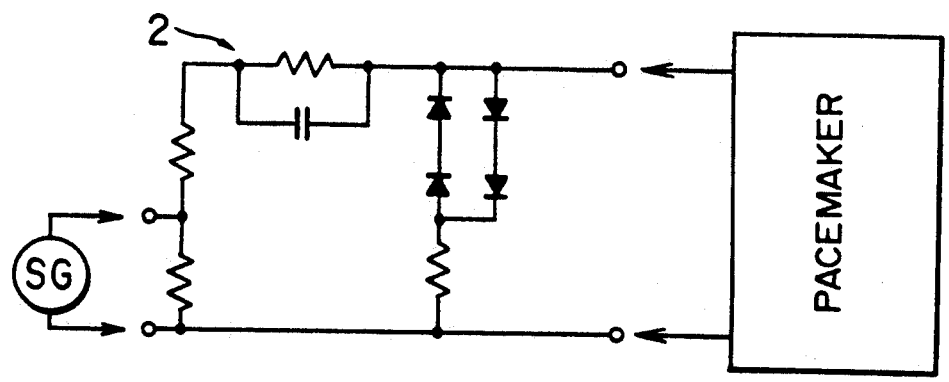
FIG. 32 is a circuit diagram of a pseudo load circuit.

The input-output terminal 4 of the circuit was connected to a pseudo load circuit 2 as shown in FIG. 32. When an evaluation test was performed, the output pulse wave height of the pacing pulse actually output to the input-output terminal was 3.2 V and the output pulse width was 2 milliseconds, if a potential of ±9 V was given as a source voltage. When the after potential at this time was measured at the point "C" in FIG. 1, the time until the potential of the after potential fell to less than 5 mV was only 85 milliseconds after the output of the pacing pulse. Therefore, about 100 milliseconds are enough time to prohibit an input to the R wave detection circuit 52 by the switching circuit 50. Further, outside of this input prohibition time, detection of the electrical activity of the heart in 2 to 20 mV can be performed with no problem at all. The conduction voltage across the emitters and bases of the transistors when such data is obtained was 625 mV, and the forward direction voltage drop of the diodes was 555 mV (when 0.7 mA). Also, the high impedance region of the output circuit was in a range of ±70 mV. Incidentally, looking at the data obtained under the same conditions as above using the output circuits of FIG. 4 and FIG. 5 instead of the output circuit 56 of FIG. 1, in the circuit of FIG. 4, the time until the potential of the after potential falls to less than 5 mV is 240 milliseconds after the output of the pacing pulse, while it is 280 milliseconds in the circuit of FIG. 5.

Similarly, a circuit evaluation test was performed using the output circuit shown in FIG. 2.

As the transistor 30, use was made of a 2SC2459, as the transistors 31 and 40, use was made of 2SA1049's, as the transistor 42, use was made of a 2SC2459, as the diodes 32 and 33, use was made of 1S953's, as the resistor 41, use was made of one of 60 Megaohms, and as the resistor 43, use was made of one of 30 Megaohms.

When a potential of ±4.5 V is given as the power source of the circuit, the output pulse wave height of the pacing pulse actually output to the input-output terminal 4 was 3.7 V and the output pulse width was 2 milliseconds. When the after potential at this time was measured at the point C in the FIG. 1, the time until the potential of the after potential fell to less than 5 mV was only 55 milliseconds after the output of the pacing pulse. Therefore, about 70 milliseconds are enough time to prohibit a input to the R wave detection circuit 52 by the switching circuit 50. Further, outside of this input prohibition time, detection of the electrical activity of the heart can be performed with no problem at all with a sensitivity of 20 mV. Also, the high impedance region of the output circuit 56a was in a range of ±200 mV.

In this way, if the above circuit is inserted into the output stage of a pacemaker, it is possible to rapidly attenuate the after potential caused after the output of a pacing pulse and thereby it is possible to reliably detect the R wave of the electrical activity of the heart without its being buried in the after potential.

Second Pacemaker

A detailed explanation will now be made of a second pacemaker according to the present invention based on the embodiments shown in the figures.

Figure 11:
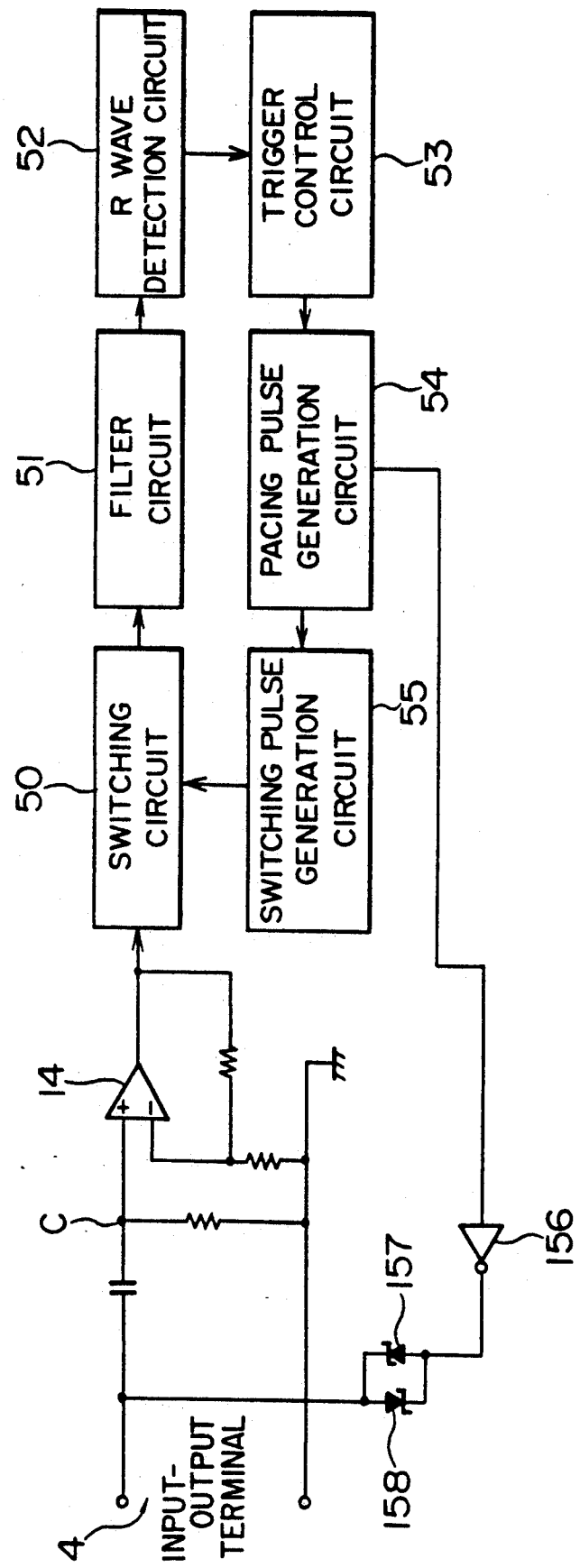
FIG. 11 and 17 are block diagrams of pacemakers according to a second aspect of the present invention.

The circuit construction of the second pacemaker according to the present invention shown in FIG. 11 is applied, for example, to an external pacemaker. The pacemaker may be applied to an internal pacemaker.

The second pacemaker according to the present invention shown in FIG. 11 has the same construction as the first pacemaker shown in FIG. 1 except for output circuit. Therefore, an explanation of the same components of the second pacemaker shown in FIG. 11 as the first pacemaker shown in FIG. 1 will be omitted.

In the present embodiment, an output circuit 156 and a pair of diodes 157 and 158 are disposed between the pacing pulse generation circuit 54 and the input-output terminal 4. This output circuit 156 has the characteristic of actively outputting a voltage until substantially 0 V or until the power source voltage. A circuit which can actively output means a circuit which has the function enabling it to discharge or suck in current in the range of the output voltage.

Figure 12:
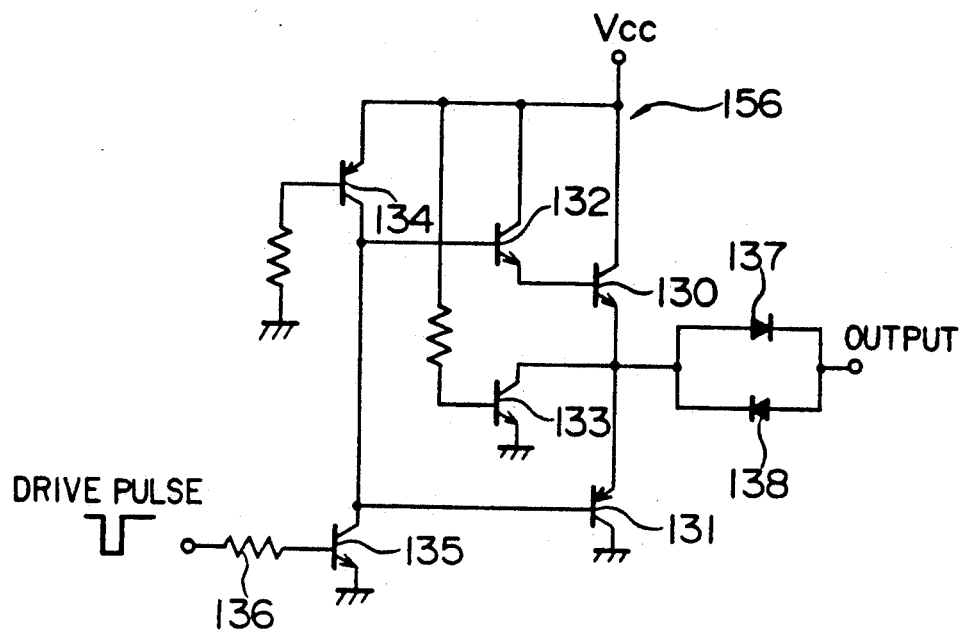
FIGS. 12 to 16 are circuit diagrams showing modifications of the output circuit shown in FIG. 11.

As an example of such an output circuit 156, as shown for example in FIG. 12, there is a circuit comprised of the six transistors 130 to 135. This circuit is a class B operation emitter-follower complementary push-pull circuit. This circuit is often used for output circuits of operational amplifiers and enables realization of a sufficiently low impedance with respect to the output side even near 0 V.

If a pacing pulse is output as a drive pulse through the resistor 136 to the base terminal of the transistor 135, a pacing pulse is output through the diode 137 among the parallel connected diodes which have opposite polarity mutually, in synchronization with the drive pulse. At this time, the impedance of the output side between the input-output terminals is made a low impedance due to the diode 138. Further, when electrical activity of the heart other than during the time of output of the pacing pulse is input to the input-output terminal 4, the parallel and reversely connected diodes 137 and 138 and the output circuit 156 function to be a high impedance in the range of voltage of the forward direction voltage of the diodes 137 and 138. In the weak voltage region where the electrical activity of the heart exhibits, the reversely connected diodes 137 and 138 and the output circuit 156 have the characteristics showing a high impedance. Therefore, in this case, the electrical activity of the heart is input to the direction of the R wave detection circuit 152 without attenuation.

Figure 13:
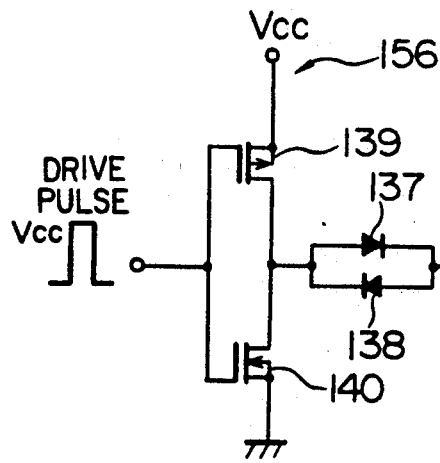
Figure 14:
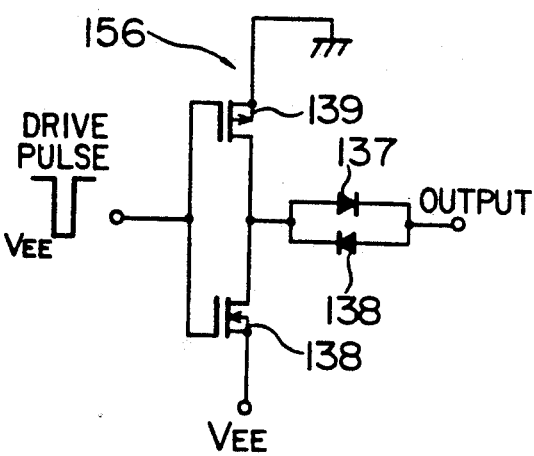

The circuit shown in FIG. 13 and FIG. 14 is a source ground complementary MOS circuit (CMOS) comprised of MOSFET's 139 and 140. In the circuit shown in FIG. 13, if one of the power source terminals is set to 0 potential, it is possible to actively output until 0 V. In the circuit shown in FIG. 14, it is possible to actively output from a negative power source voltage to 0 V.

In the circuits shown in FIG. 13 and FIG. 14, if a pacing pulse is input as a drive pulse to the MOSFET's 139 and 140, a pulse will be output through the diode 137 among the parallel connected diodes which have opposite polarity mutually, synchronization with the drive pulse. At this time, the impedance of the output side is made a low impedance through the diode 138.

Figure 15:
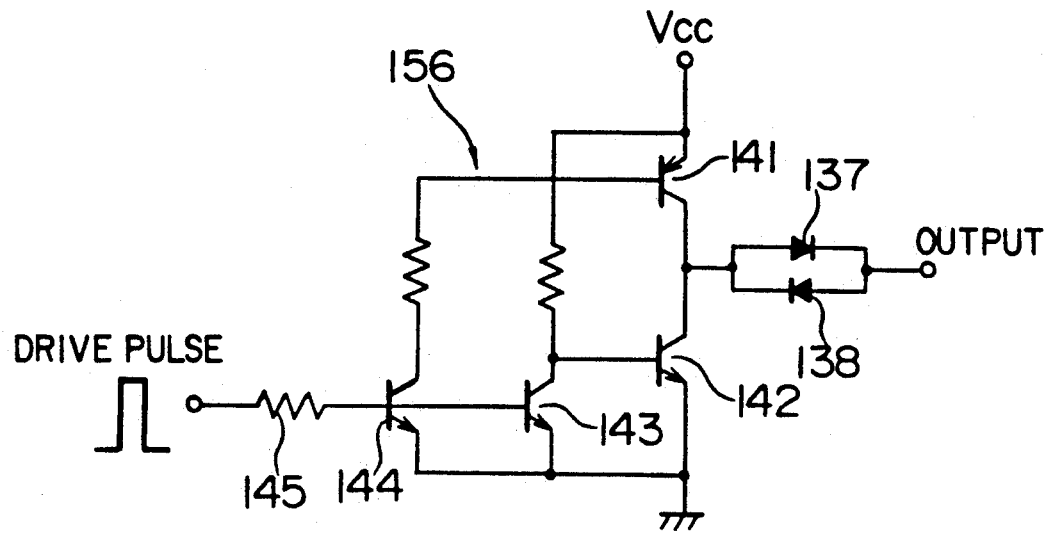
Figure 16:
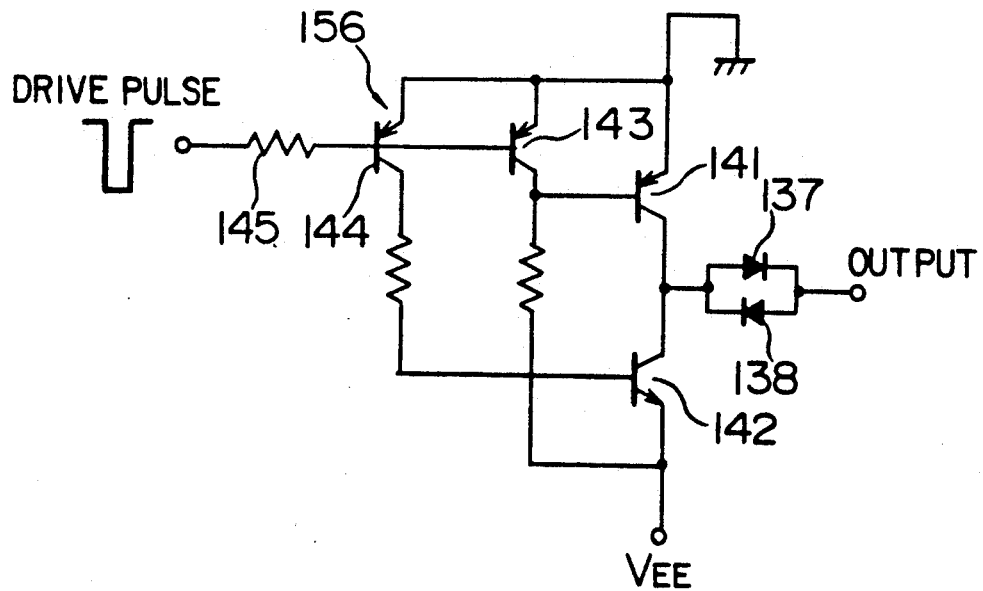

The circuits shown in FIG. 15 and FIG. 16 are collector output circuits which are comprised of the four transistors 141 to 144. In the circuit of FIG. 15, positive output is possible until close to 0 V (about 20 mV). In the circuit of FIG. 16, negative output is possible to close to 0 V.

In both circuits, if a drive pulse is output as a pacing pulse to the transistors 143 and 144 through the resistor 145, then a pulse is output through the diode 137 among the parallel connected diodes which have opposite polarity mutually, in synchronization with the drive pulse. At this time, the impedance of the output side is made a low impedance through the diode 138.

In this way, according to a circuit in which an output circuit 156 which can actively output to substantially 0 V or to substantially the power source voltage is connected to an input-output terminal 4 through the mutually reversely connected diodes 137 and 138, if the potential of the signal sent through the input-output terminal 4 is in a predetermined range within the forward direction voltage of the diode, the input-output terminal 4 is set to a high impedance of at least more than 5 kiloohms, preferably more than 10 kiloohms. While it is set to a low impedance when the potential of the signal is outside of that range. Here, a predetermined range near 0 V means a range narrower than the range of −600 to +600 mV, preferably the voltage range of the electrical activity of the heart, that is, the range of near ±20 mV (−20 to +20 mV).

The range where the output impedance becomes high can be changed by selecting the types of the parallel, reversely connected diodes 137 and 138. That is, if use is made of usual silicon diodes as the diodes 137 and 138, then a region where the impedance is extremely high can be obtained in the output range of ±0.7 V (range of −0.7 to +0.7 V). If use is made of Schottky diodes as the diodes 137 and 138, extremely high output impedance regions can be obtained in the output range of ±0.2 V to ±0.5 V.

In addition to the above-mentioned circuits, various types of output circuits able to actively output to 0 V or substantially the power source voltage may be considered. These circuits of course can also be applied as the output circuits of the present invention.

However, open collector, open drain, switch, and other types have extremely high impedances when these are turned off and do not have the ability to discharge the after potential, so cannot be used. Further, emitter-ground complementary push-pull types have high impedances unless current constantly is passed through them, so are not suited to pacemakers.

According to the output circuit 156 and the reversely connected diodes 137 and 138 according to the present invention, it is possible to efficiently detect the R wave from the input-output terminal 4 while a pacing pulse is not being generated and, when a pacing pulse is output from the input-output terminal 4, the after potential of the pacing pulse is rapidly attenuated, so the time when the input to the R wave detection circuit must be stopped due to the after potential becomes extremely short and the failure to detect R waves is reduced. Further, the output circuit does not use any switches, so there are no sharp fluctuations of the potential caused by turning switches on and off.

Note that the present invention is not limited to the above-mentioned embodiments and can be modified in various ways in the scope of the invention.

Figure 17:
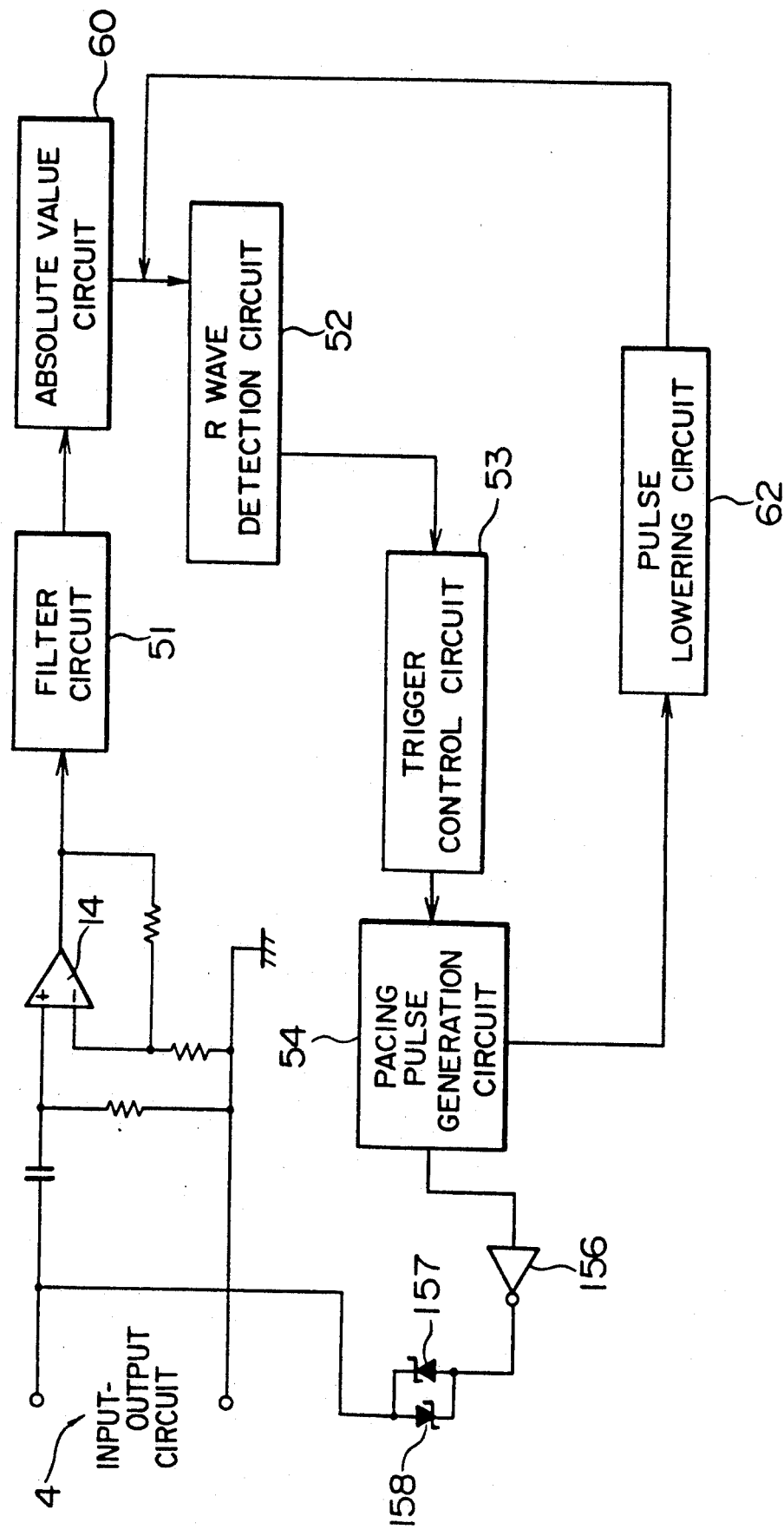

For example, the pacemaker according to the present invention is not limited in terms of the circuit constructions other than the output circuit 156 and the diodes 137 and 138 and for example may be of the circuit construction shown in FIG. 17.

In the circuit shown in FIG. 17, there is no need to provide the switching pulse generation circuit 55 and the switching circuit 50 shown in FIG. 11. Instead, provision may be made of an absolute value circuit 60 and a pulse lowering circuit 62.

The absolute value circuit 60 and the pulse lowering circuit 62 sown in FIG. 17 are the same circuit as the circuit 60 and 62 shown in FIG. 6 and the explanation thereof is eliminated.

If this construction is adopted, even if a switch element is not used, there is no longer any erroneous detection of the pacing pulse and the after potential as an R wave by the R wave detection circuit 52 comprised of a comparison circuit. Further, even if a switch element is used, the pulse due to the leakage current etc. does not have any effect on the detection of the R wave. The reason is that the switch operation is performed at the negative side opposite in polarity to the signal to be detected (no positive noise is produced).

In the circuit of the pacemaker too, if the output circuit 156 and diodes 137 and 138 are connected between the pacing pulse generation circuit 54 and input-output terminal 4, the function is the same as the embodiment shown in FIG. 11. In particular, in this embodiment, even if a switching circuit is not used, there is no longer any erroneous detection of the pacing pulse and the after potential as an R wave by the R wave detection circuit 52 comprised of a comparison circuit and also the pulse lowering time T by the pulse lowering circuit 62 may be shortened, so this is convenient.

Figure 18:
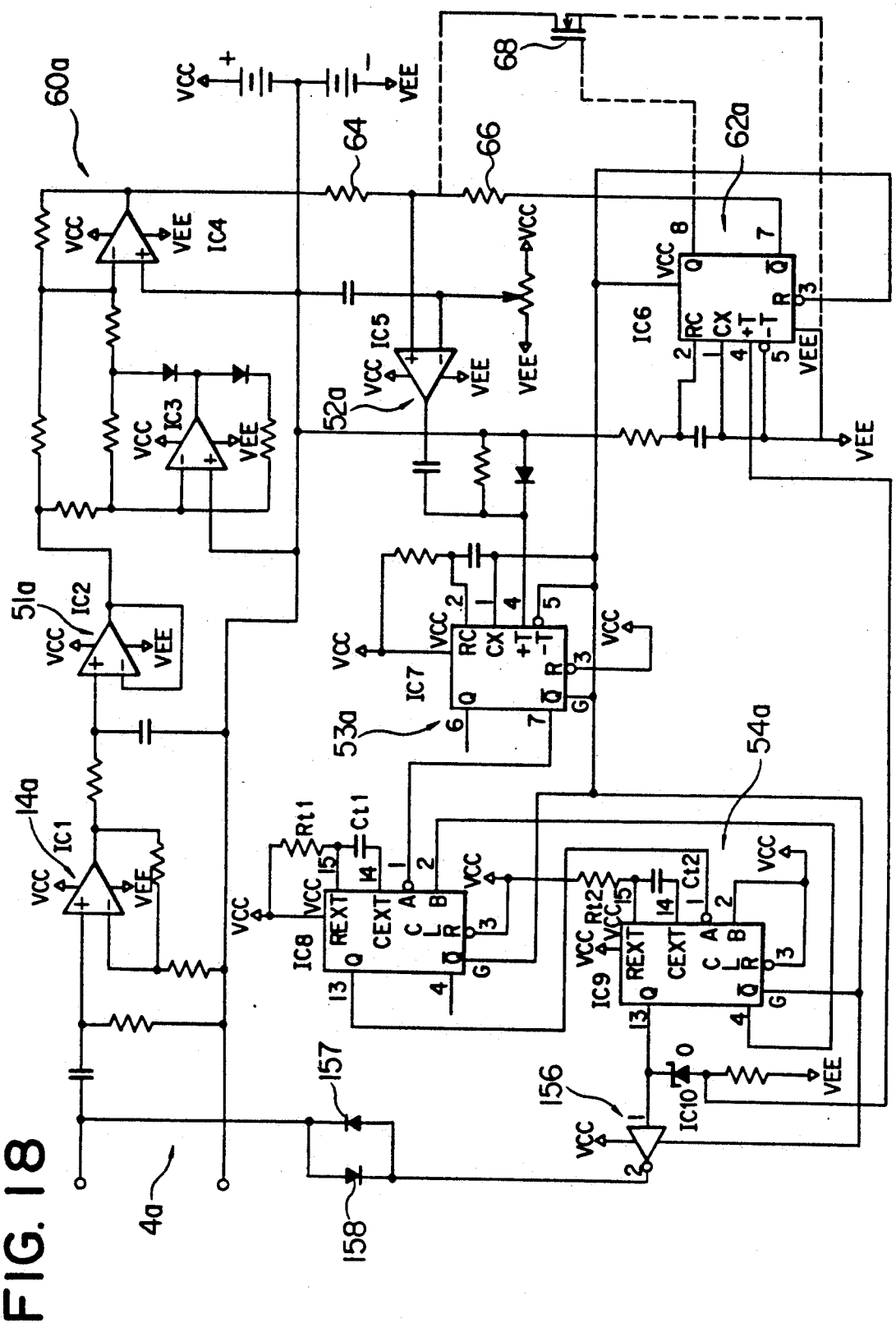
FIG. 18 is a circuit diagram in greater detail than the block diagram of FIG. 17.

A more detailed circuit diagram of the pacemaker shown in FIG. 17 is shown in FIG. 18.

In FIG. 18, the reference 4a is an input-output terminal, and 14a is an amplification circuit which is comprised of an operational amplifier and has an amplification rate of several 100. Reference 51a is a filter, which is, for example, comprised of the low pass type and has a buffer of an operational amplifier. Reference 60a is an absolute value circuit, which absolute value circuit is comprised of a typical circuit based on two operational amplifiers and outputs an output signal on a positive polarity. Reference 52a is a comparison circuit, which is comprised of an operational amplifier performing a comparator operation and is designed that the comparison potential is finely adjusted to the positive side. In the comparison circuit 52a, when a potential higher than the comparison potential is input, an output signal of a positive polarity is output, while at other times, a negative output signal is produced. The output from the absolute value circuit 60a is connected to the input end of the comparison circuit 52a through a resistor 64.

Reference numeral 62a is a switch signal generator, which operates with a negative power source. The switch signal generator is comprised of a one-shot multi-vibrator which shifts the level of the pacing output to make it a negative level and which enables, in synchronization with the rise of the pacing output, an output from 0 to the negative side from the output "$\bar{Q}$" and an output from the negative side to 0 from the output "Q", so that the output starts to appear in synchronization with the rise of the pacing pulse and the output is stopped after tens to hundreds of milliseconds or so. The output side of the switch signal generator 62a is connected to the input side of the comparison circuit 52a through a resistor 66. The switch signal generator 62a and the resistor 66 comprise a pulse lowering circuit 62 as shown in FIG. 17. Instead of the resistor 66, use may be made of an FET 68. Further, instead of the resistor 66 or the FET, an open collector or an open drain transistor may be connected between the output of the signal generator 62a and the input end of the comparison circuit 52a, the emitter or the source of which may be connected to the negative power source and the base or gate of which may be switched by the negative potential.

Reference numeral 53a in FIG. 18 is a one-shot multi-vibrator which stops the detection for approximately 250 to 300 milliseconds after detection of the electrical activity of the heart. This multi-vibrator 53a has the function of receiving the output signal of the comparison circuit 52a, sending the reset signal to the pacing pulse generation circuit 54a, and resetting a timer for calculating the pulse interval of a next pacing pulse to be output from the pacing pulse generation circuit 54a. That is, the multi-vibrator 53a corresponds to the trigger control circuit shown in FIG. 17.

Note that the pacing pulse generation circuit 54a is designed to set the pulse interval and the pulse width by t1 and t2. Reference numeral 156 is a pacing pulse output circuit.

As clear from the above explanation, according to second pacemaker of the present invention, when just the electrical activity of the heart is input to the input-output terminal, since the electrical activity of the heart is in the range of ±20 mV, which is a relatively low range of voltage near 0 V, the output circuit and the reversely connected diodes function so that the input-output terminal is set to a high impedance. Therefore, the electrical activity of the heart will be input to the R wave detection circuit without attenuation. Further, when the pacing pulse is output from the input-output terminal, the after potential is in an extremely high voltage range compared with the electrical activity of the heart, so the output circuit and the reversely connected diodes function so that the input-output terminal is set to a low impedance. By this, the after potential is rapidly attenuated to within the voltage range of the electrical activity of the heart near 0 V determined by the forward direction voltage characteristic of the diodes and then gradually is attenuated in accordance with a time constant. Therefore, the time when the input to the R wave detection circuit must be stopped due to the after potential becomes extremely short and the failure of detection of the R wave decreases. Further, there are no rapid fluctuations in the potential arising due to the on-off operation of a switch.

An explanation will now be made of the present invention using more detailed examples, however, the present invention is not limited to these examples.

A circuit as shown in FIG. 11 was prepared. As the output circuit 56 shown in FIG. 11, use was made of a circuit of the construction shown in FIG. 12. As the transistors 130, 132, 133, and 135, use was made of 2SC2459's, as the transistors 131 and 134, use was made of 2SA1049's, as the diodes 137 and 138, use was made of Schottky barrier diodes (IS2181), and as the resistor 136, use was made of one of 100 kiloohms.

The input-output terminal 4 of the circuit was connected to a pseudo load circuit 2 as shown in FIG. 32. When an evaluation test was performed, the output pulse wave height of the pacing pulse actually output to the input-output terminal 4 was 3.8 V and the output pulse width was 2 milliseconds, if a potential of +4.5 V and −3 V was given a source voltage. When the after potential at this time was measured at the point "C" in the FIG. 11, the time until the potential of the after potential fell to less than 5 mV was only 55 milliseconds after the output of the pacing pulse. Therefore, about 70 milliseconds are enough time to prohibit an input to the R wave detection 52 by the switching circuit 50. Further, outside of this input prohibition time, detection of the electrical activity of the heart in 2 to 20 mV can be performed with no problem at all.

In this way, if the above circuit is inserted into the output stage of a pacemaker, it is possible to rapidly attenuate the after potential caused after the output of a pacing pulse and thereby it is possible to reliably detect the R wave of the electrical activity of the heart without its being buried in the after potential.

Third Pacemaker

A detailed explanation will now be made of a third pacemaker according to the present invention based on the embodiments shown in the figures.

Figure 19:
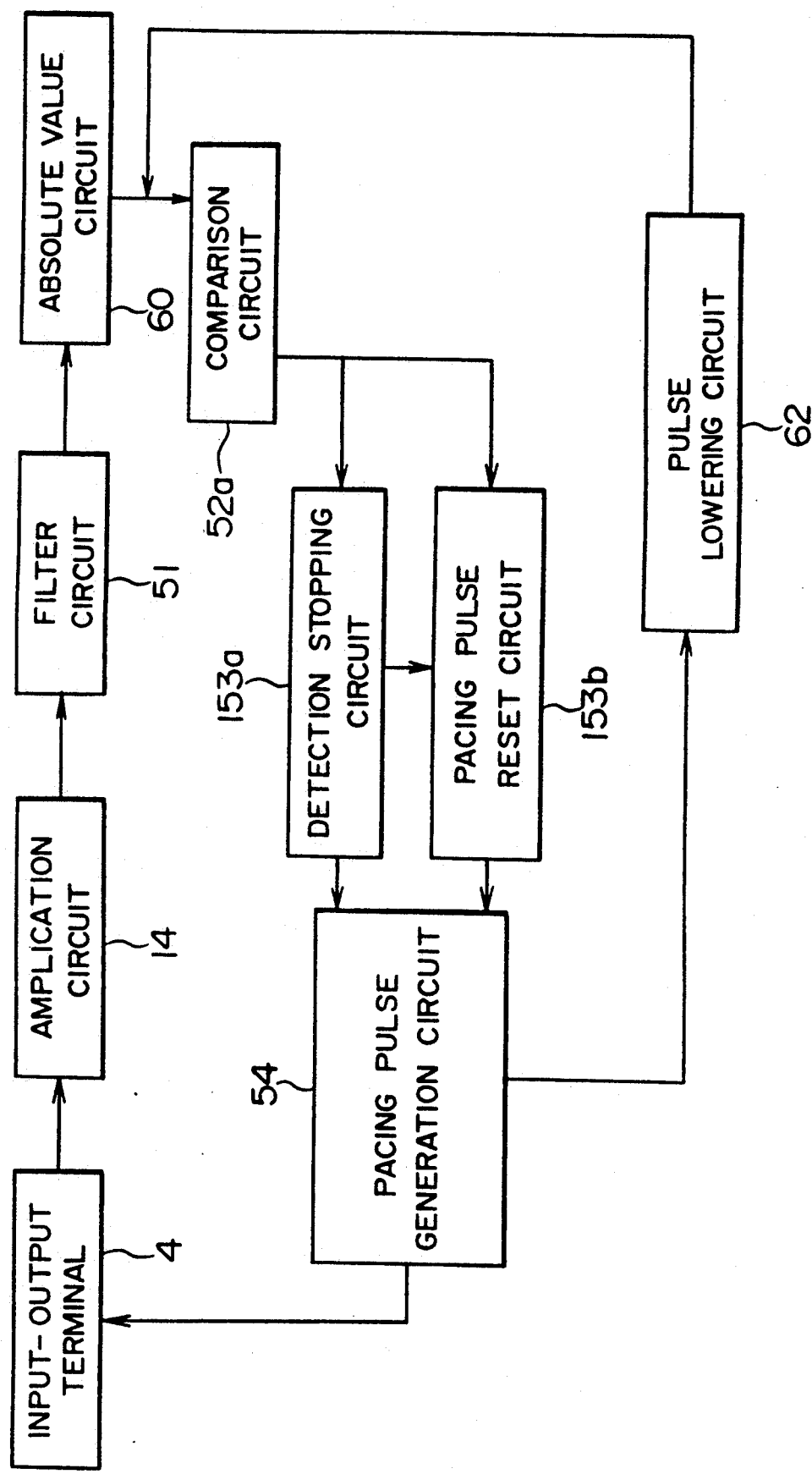
FIG. 19 is a block diagram of a pacemaker according to a third aspect of the present invention.

The circuit construction of the third pacemaker according to the present invention shown in FIG. 19 is applied, for example, to an external pacemaker. The pacemaker may be applied to an internal pacemaker.

The pacemaker of the embodiment shown in FIG. 19 has the same construction basically as the first pacemaker shown in FIG. 6 except for output circuit. Therefore, an explanation of the same components of the third pacemaker shown in FIG. 19 as the first pacemaker shown in FIG. 6 will be omitted.

Figure 33:
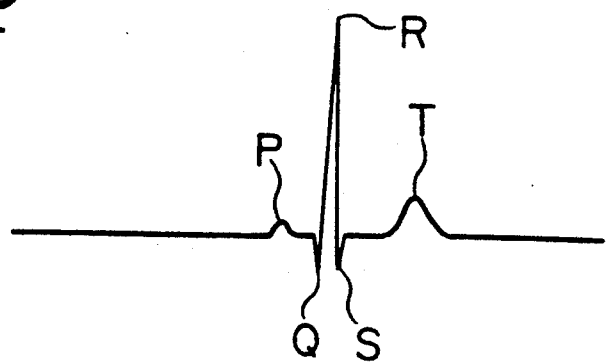
FIG. 33 is a schematic view of an electrocardiogram.
Figure 34:
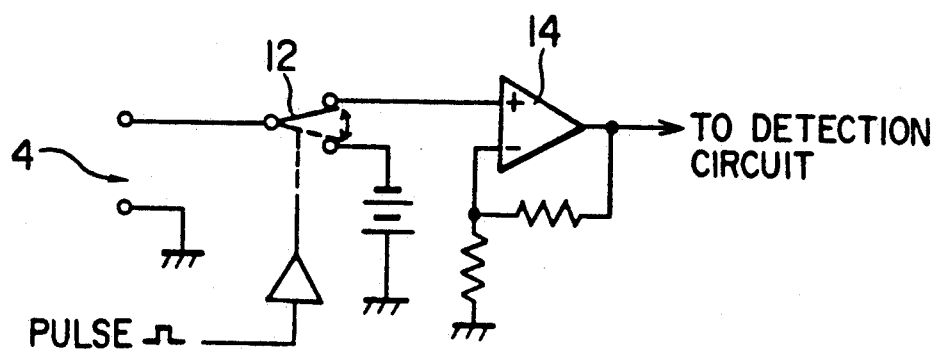
FIGS. 34 to 38 are circuit diagrams of switching circuits used in pacemakers.
Figure 35:
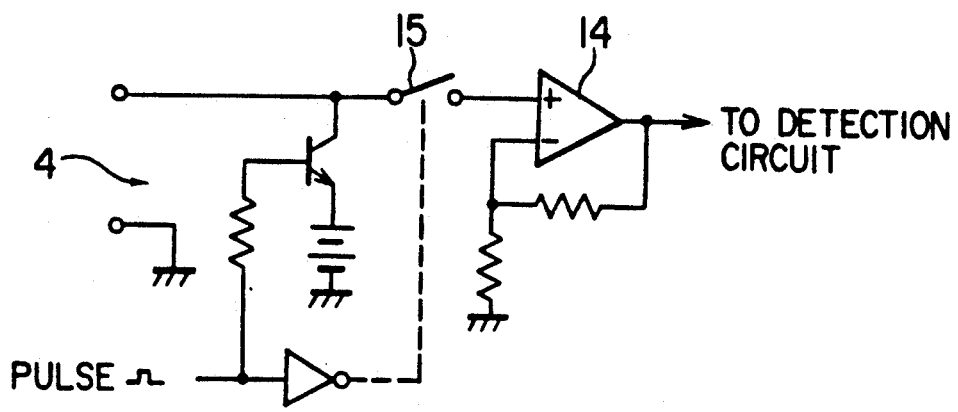
Figure 36:
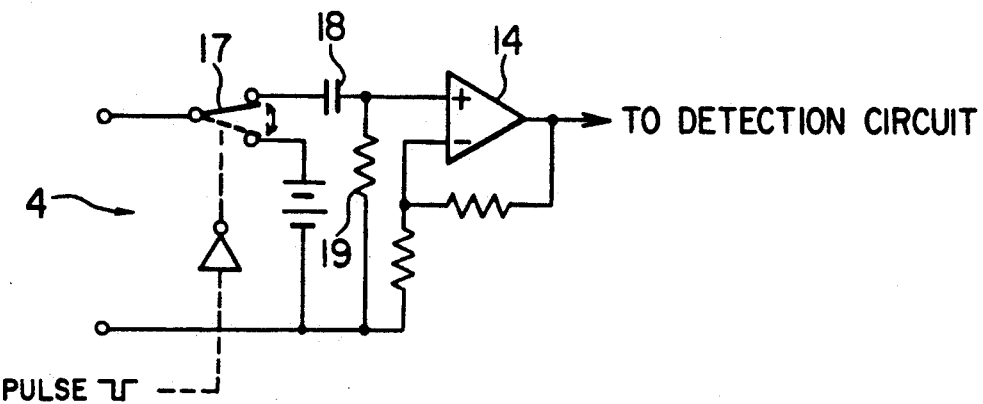
Figure 37:
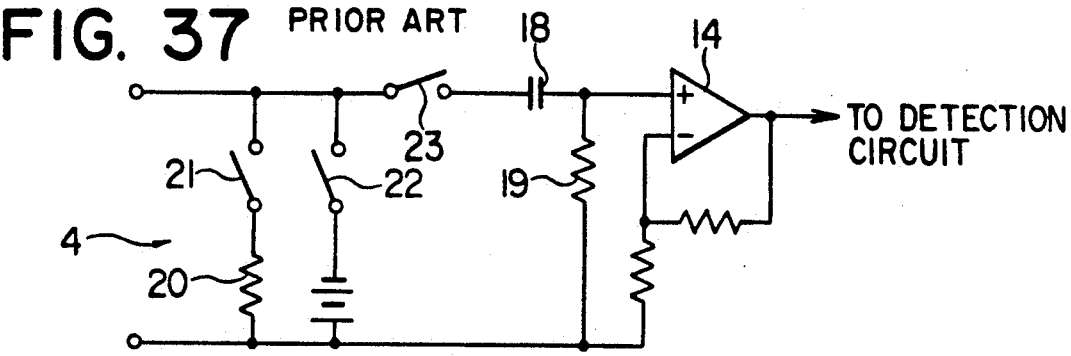
Figure 38:
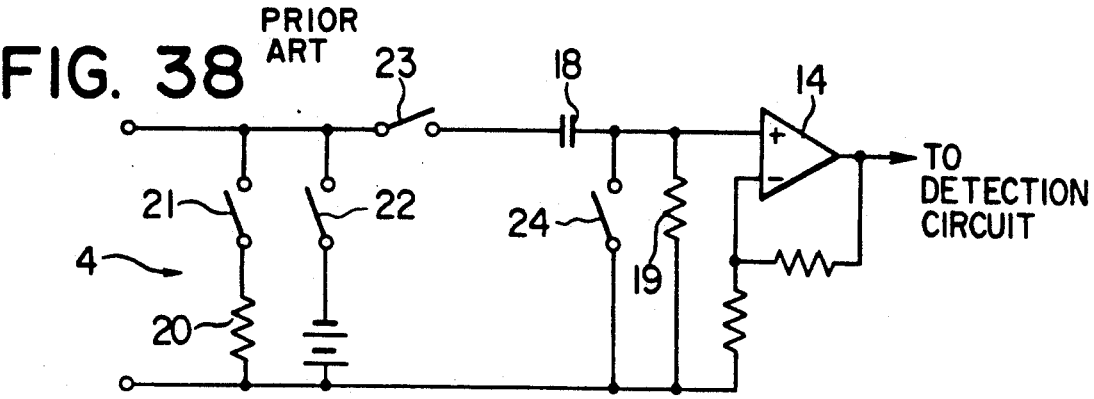
Figure 39A:
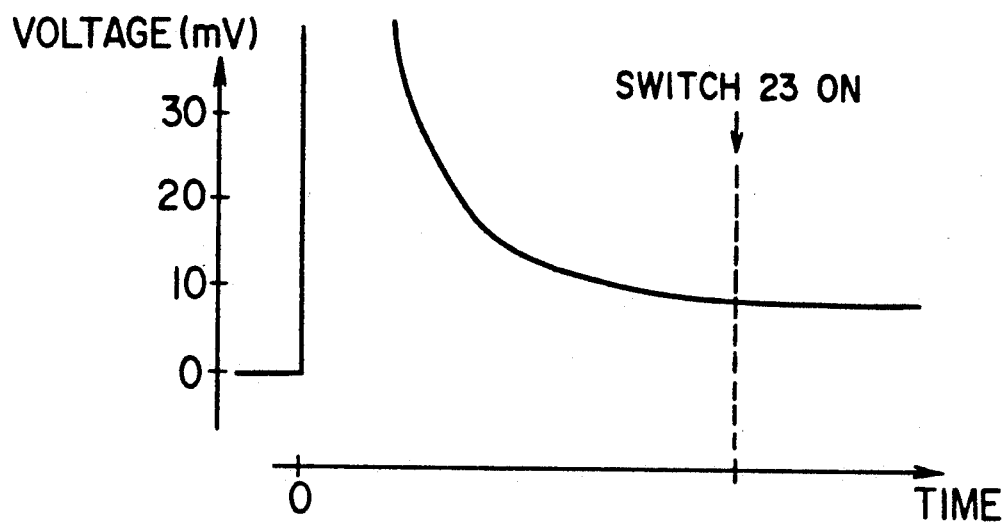
FIGS. 39(A) and 39(B) are graphs showing the effect of the after potential in a conventional pacemaker.
Figure 39B:
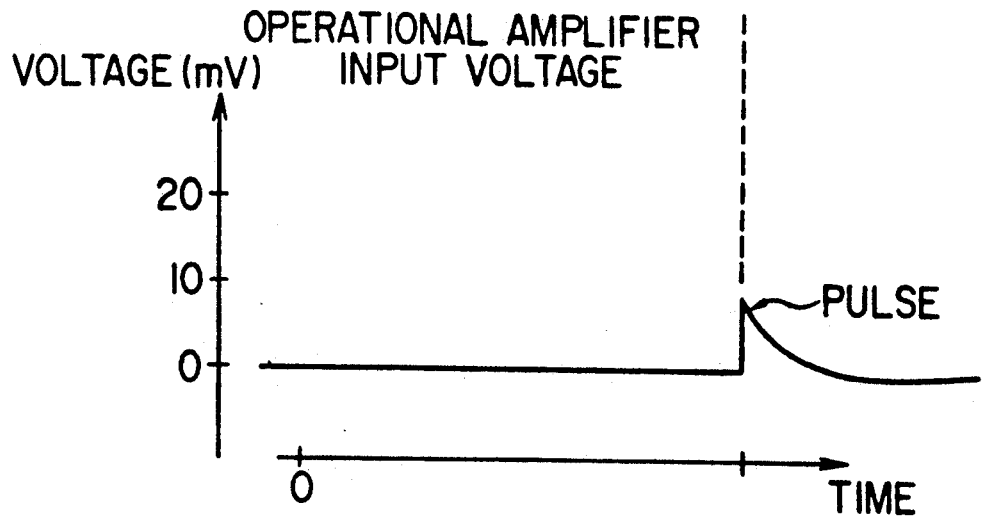

A detection stopping circuit 153a and a pacing pulse reset circuit 153b are corresponding to the trigger control circuit 53 shown in FIG. 6. The detection stopping circuit 153a is a circuit for stopping the detection by the comparison circuit 52a for a predetermined time after detection of an R wave of a electrical activity of the heart by the comparison circuit 52a. This predetermined time is a time sufficient for preventing detection of the S wave, T wave, or premature contraction etc. after the R wave of the electrical activity of the heart as shown in FIG. 33 and in general is 250 to 300 milliseconds.

The detection stopping circuit 153a is connected to the pacing pulse reset circuit 153b and the pacing pulse generation circuit 54. The pacing pulse generation circuit 54 is connected to the input-output terminal 4.

The pacing pulse generation circuit 54 is a circuit which generates a pacing pulse in an adjustable predetermined cycle of time. When a R wave is detected by the comparison circuit 52a, the pacing pulse reset circuit 153b resets the pacing pulse and keeps the pacing pulse from being output toward the input-output terminal 4. Further, after the R wave is detected, if the R wave is not detected by the comparison circuit 52a for a predetermined time where the next R wave should be detected, a pacing pulse is output from the pacing pulse generation circuit 54 to the input-output terminal 4. When an R wave is not detected by the comparison circuit 52a for a predetermined time after the output of the pacing pulse, a further pacing pulse is output. This operation continues until the R wave is detected by the comparison circuit 52a. The input-output terminal 4, as mentioned earlier, is connected to a catheter having an electrode embedded in the heart, so the heart can be paced by the pacing pulse output from the input-output terminal 4.

This pacing generation circuit 54 is also connected to a pulse lowering circuit 62. The output of the pulse lowering circuit 62 is connected to the input side of the comparison circuit 52a. The pulse lowering circuit 62 has a function so that when a pacing pulse from the pacing generation circuit 54 is output toward the input-output terminal 4, a lowering pulse is added to the unipolarity input signal entering from the absolute value circuit 60 to the comparison circuit 52a for a predetermined time. The lowering pulse has a polarity opposite to the unipolarity of the input signal from the absolute value circuit 60 and has a potential larger than the input signal. Thereby, the input of an input signal of larger than a predetermined value to the comparison circuit 52a can be prevented.

When the input signal from the absolute value circuit 60 is of a positive polarity, a negative polarity pulse, i.e., a polarity opposite to the positive one, shown in FIG. 9(B), is input to the input side of the comparison circuit 52a. The width (time) T of the negative polarity pulse is preferably a width of more than the time of the effect of the pacing pulse and the after potential input from the input-output terminal 4. The time T in general is 20 to 150 milliseconds. Further, the negative polarity pulse voltage V is preferably larger than the maximum waveform potential V2 of the pacing pulse and after potential shown in FIG. 9(A) passing through the amplification circuit 14, filter circuit 51, and absolute value circuit 60. At the input side of the comparison circuit 52a, the pulse shown in FIG. 9(B) is applied to the wave-form shown in FIG. 9(A) corresponding to the pacing pulse and the after potential and becomes the waveform shown in (C) of the figure.

Even if the wave-form shown in (C) of the figure is input to the comparison circuit 52a, the wave-form corresponding to the pacing pulse and the after potential is sufficiently lowered by the lowering pulse, so the comparison circuit 52a which detects signals of a positive polarity greater than the predetermined value will not erroneously detect a signal as an R wave. In the above explanation of the operation, the case was of a positive output of the absolute value circuit 60, but even if the circuit is constructed with a negative output of the absolute value circuit 6 and the subsequent polarities all reversed, the circuit operates in the exactly same way and it is sufficient to read lowering as raising. According to the invention, "lowering" is used to include the meaning of "raising" in this specification.

If the above-mentioned construction is adopted, even if a switch element is not used, there is no longer any erroneous detection of the pacing pulse and the after potential by the comparison circuit 52a as an R wave. Further, even if a switch element is used, the pulse due to the leakage current etc. does not have any effect on the detection of the R wave. The reason is that the switch operation is performed at the negative side opposite in polarity to the signal to be detected (no positive noise is produced).

Figure 20:
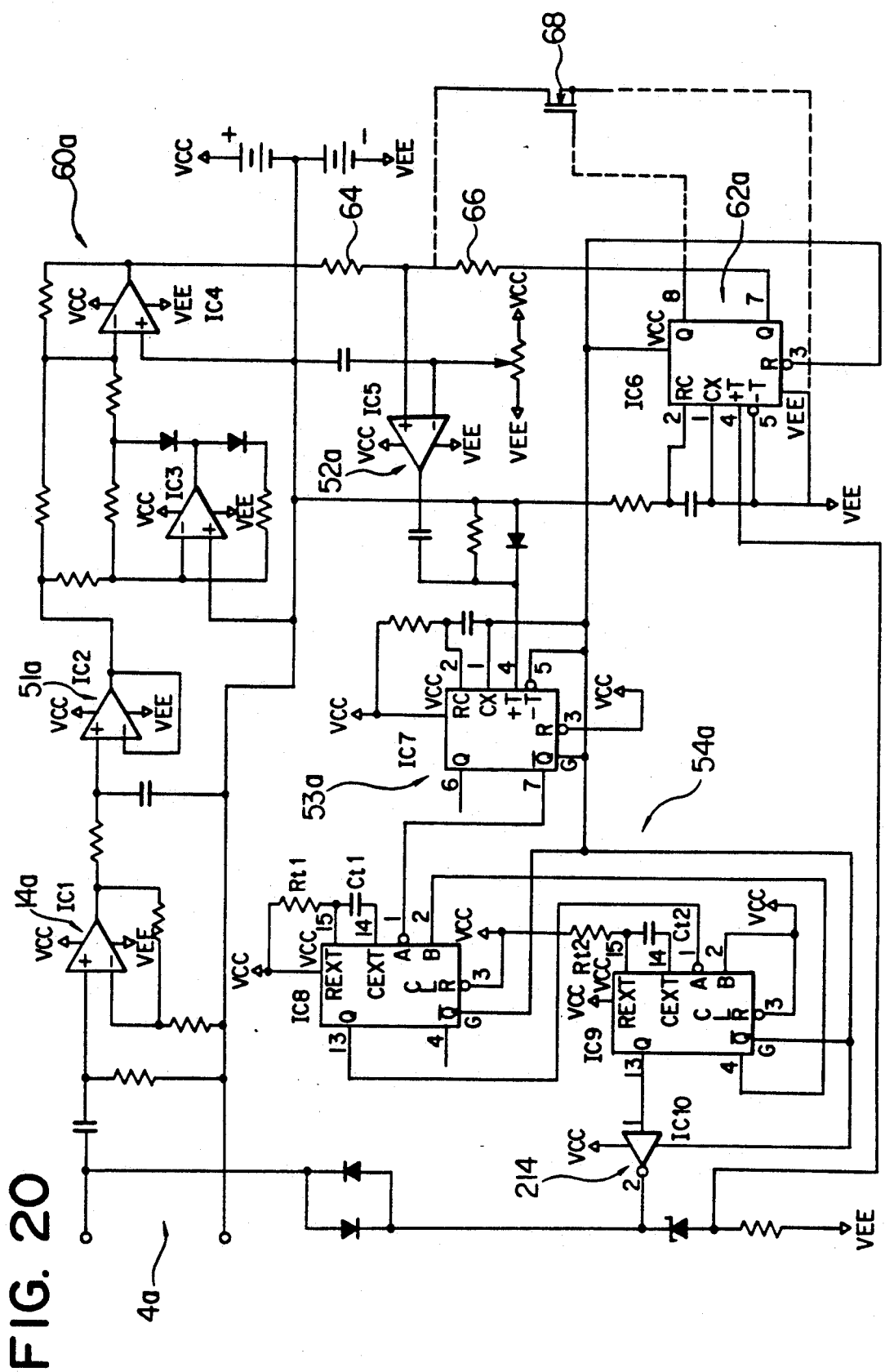
FIGS. 20 is a circuit diagram in greater detail than the block diagram of FIG. 19.

A more detailed circuit diagram of the pacemaker shown in FIG. 19 is shown in FIG. 20.

In FIG. 20, the reference 4a is an input-output terminal, and 14a is an amplification circuit which is comprised of an operational amplifier and has an amplification rate of several 100. Reference 51a is a filter, which filter is, for example, of the low pass type and has a buffer of an operational amplifier. Reference 60a is an absolute value circuit, which is comprised of a typical circuit based on two operational amplifiers and outputs an output signal of a positive polarity. Reference 52a is a comparison circuit, which is comprised of a operational amplifier performing a comparator operation and is designed that the comparison potential is finely adjusted to the positive side. In the comparison circuit 52a, when a potential higher than the comparison potential is input, an output signal of a positive polarity is output, while at other times, a negative output signal is produced. The output from the absolute value circuit 5a is connected to the input end of the comparison circuit 52a through a resistor 64.

Figure 21:
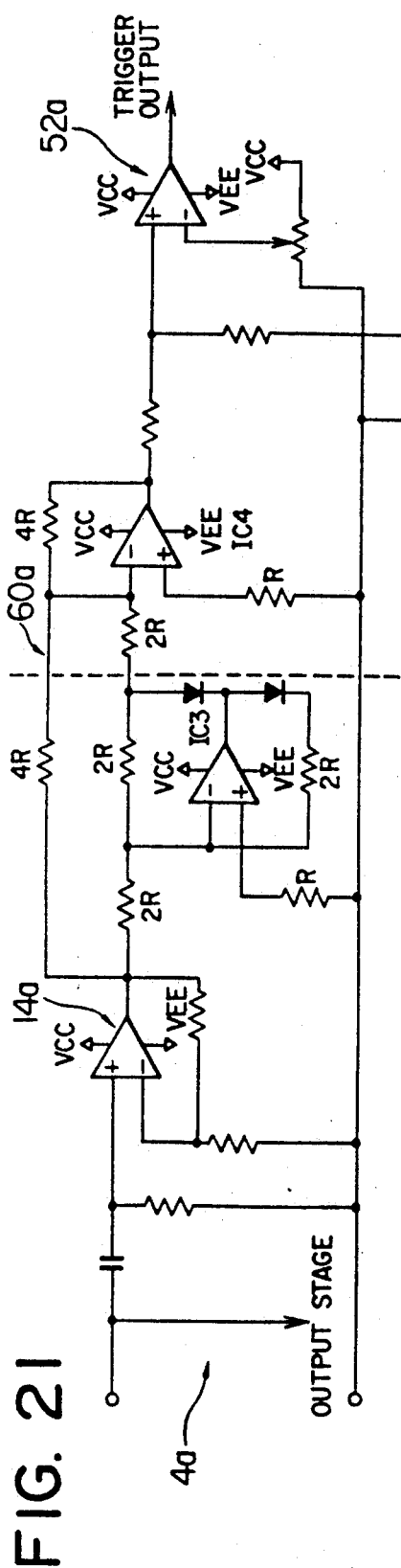
FIGS. 21 and 22 are circuit diagrams showing modifications of a comparison circuit shown in FIG. 19.
Figure 22:
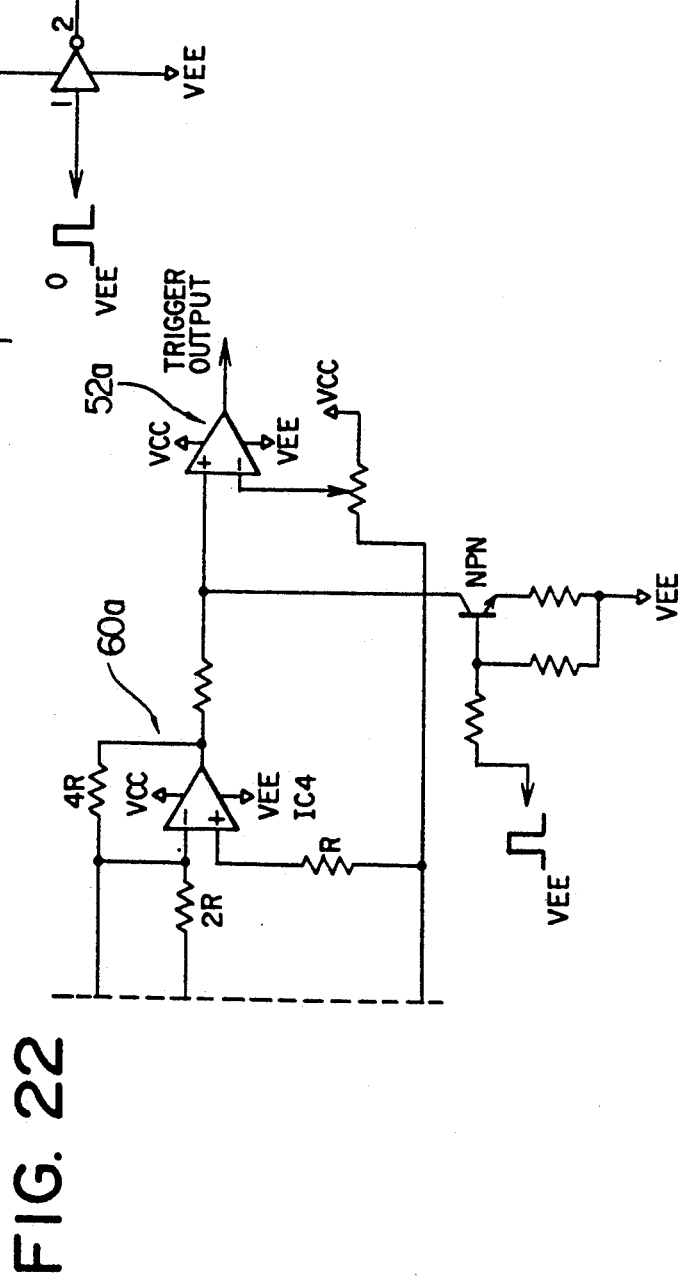

Reference numeral 62a is a switch signal generator, which operates with a negative power source. The switch signal generator is comprised of a one-shot multi-vibrator which shifts the level of the pacing output to make it a negative level and which enables, in synchronization with the rise of the pacing output, an output from 0 to the negative side from the output "$\overline{Q}$" and an output from the negative side to 0 from the output "Q", so that the output starts to appear in synchronization with the rise of the pacing pulse and the output is stopped after tens to hundreds of milliseconds or so. The output side of the switch signal generator 62a is connected to the input side of the comparison circuit 52a through a resistor 66. The switch signal generator 62a and the resistors 64 and 66 comprise a pulse lowering circuit 62 as shown in FIG. 19. Instead of the resistor 66, use may be made of an FET 68 and the FET be made to operate when receiving an output "Q" of the generator 62a. Further, as shown in FIG. 21 and FIG. 22, an open collector or an open drain transistor is connected from the output of the signal generator 62a to the input end of the comparison circuit 52a, the emitter or the source of which are connected to the negative power source and the base or gate of which can be switched by the negative potential.

Reference numeral 53a in FIG. 20 is a one-shot multi-vibrator which stops the detection for approximately 250 to 300 milliseconds after detection of the electrical activity of the heart. This multi-vibrator 53a has the function of receiving the output signal of the comparison circuit 52a, sending the reset signal to the pacing pulse generation circuit 54a, and resetting so that the pacing pulse from the pacing pulse generation circuit 54a is not output to the input-output terminal 4a. That is, the multi-vibrator 53a corresponds to the detection stopping circuit 153a and the pacing pulse reset circuit 153b shown in FIG. 19.

Note that the pacing pulse generation circuit 54a is comprised of two one-shot multi-vibrators and is designed to set the pulse interval and the pulse width by t1 and t2. Reference numeral 214 is a pacing pulse output stage.

The present invention is not limited to the above-mentioned embodiments and can be modified in various ways in the scope of the invention.

According to the third pacemaker of the present invention, it is possible to prevent the comparison circuit from detecting the pacing pulse and the following after potential without provision of a switching circuit to prevent detection of the pacing pulse. Further, even if use is made of a switching circuit, the pulse due to the leakage current etc. does not have an effect on the detection of the R wave.

Further, according to the circuit of the third pacemaker of the present invention, a production efficiency of the pacemaker is improved.

An explanation will now be made of the present invention using more detailed examples, however, the present invention is not limited to these examples.

A circuit as shown in FIG. 20 was prepared.

As the amplification circuit 14a, use was made of an operational amplifier having a 201 fold amplification rate and comprised of an LM4250(IC1). As the filter circuit 51a, use was made of a low pass type having a buffer of an operational amplifier (IC2=LM4250). As the absolute value circuit 60a, use was made of a typical type based on two operational amplifiers (IC3,4=LM4250) having a positive output. As the comparison circuit, use was made of an operational amplifier (IC5=LM4250) made to perform a comparator operation and finely adjusting the comparison potential to the positive side. As the switch signal generator 62a operating with a negative power source, use was made of a one-shot multi-vibrator (IC6=COMS4538) which shifts the level of the pacing output to make it a negative level and which enables, in synchronization with the rise of the pacing output, an output from 0 to the negative side from the output "$\overline{Q}$" and an output from the negative side to 0 from the output "Q". The one-shot multi-vibrator 62a was designed that the output started to appear in synchronization with the rise of the pacing pulse and the output was stopped after approximately 60 milliseconds.

As the one-shot multi-vibrator 53a, use was made of one which detects the electrical activity of the heart and then stops the detection for 250 to 300 milliseconds. As the pacing pulse generation circuit 54a, use was made of one which is made to set the pulse interval and pulse width by t1 and t2.

To the input-output terminal of the circuit was connected a pseudo load circuit 2 as shown in FIG. 32. When this was operated, the pacing pulse and after potential were effectively eliminated and there was no noise of switching.

FOURTH PACEMAKER

A detailed explanation will now be made of a fourth pacemaker according to the present invention based on the embodiments shown in the figures.

Figure 23:
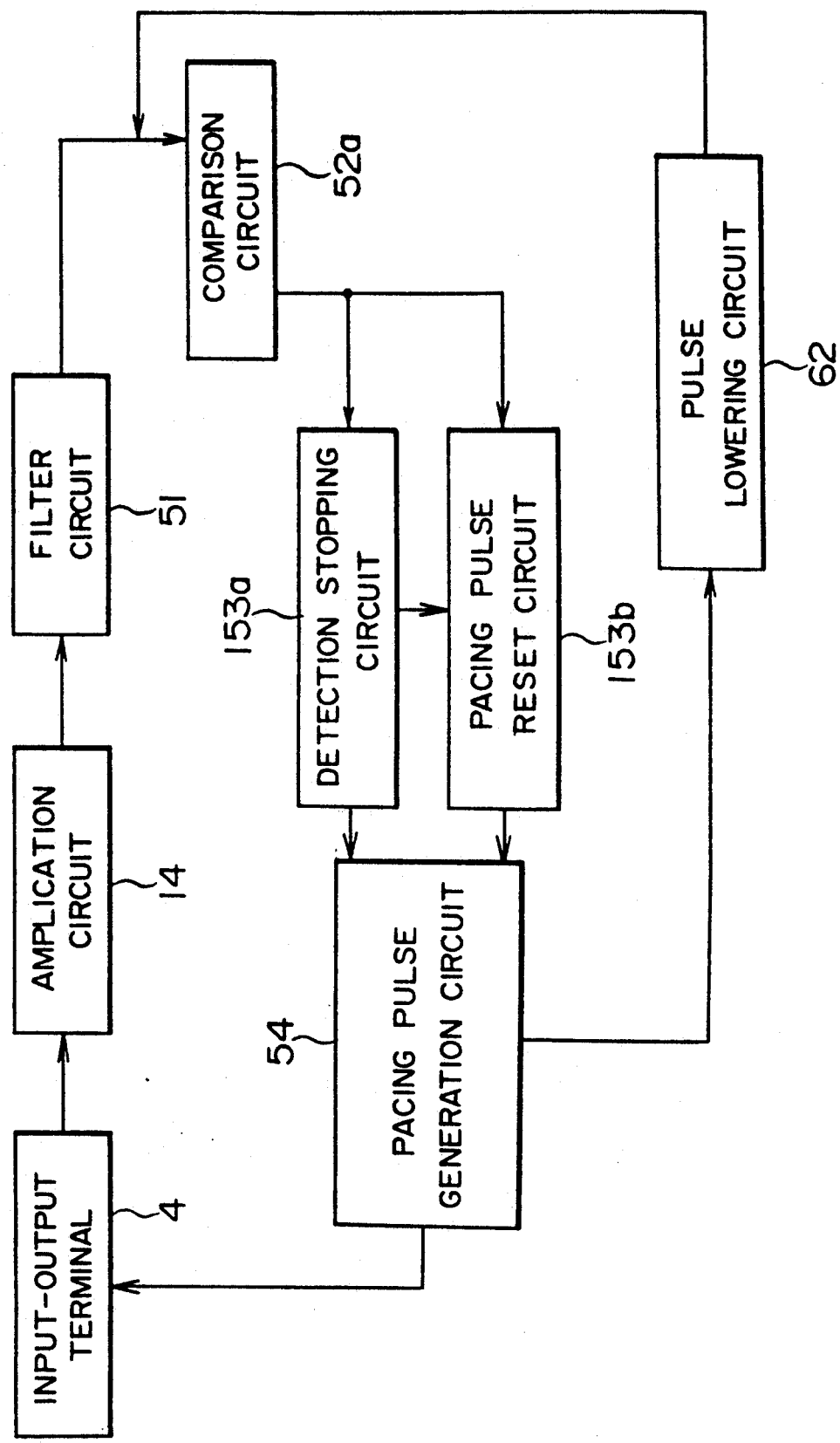
FIG. 23 is a block diagram of a pacemaker according to a fourth aspect the present invention.

The circuit construction of the pacemaker according to the first embodiment of the present invention shown in FIG. 23 is applied, for example, to an external pacemaker. The pacemaker may be applied to an internal pacemaker.

The pacemaker of the embodiment shown in FIG. 23 has the same construction as the third pacemaker shown in FIG. 19 except that the fourth pacemaker does not have the absolute value circuit 60 of the third pacemaker. Therefore, an explanation of the same components of the fourth pacemaker shown in FIG. 23 as the third pacemaker shown in FIG. 19 will be omitted.

Figure 24:
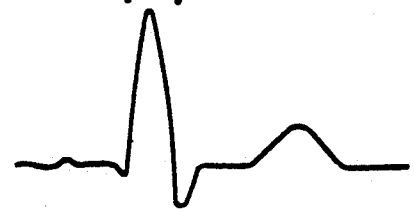
FIGS. 24(A)-24(C) and 25(A)-25(C) are schematic views showing signal wave-forms in the middle of the circuits shown in FIG. 23.
Figure 25A:
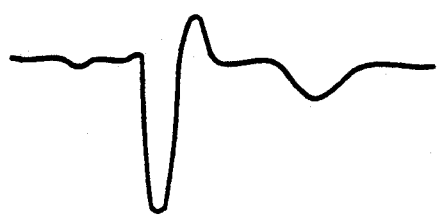
Figure 24:
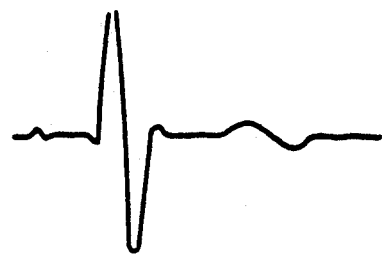
Figure 25B:
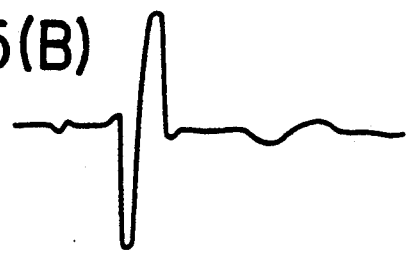
Figure 24C:
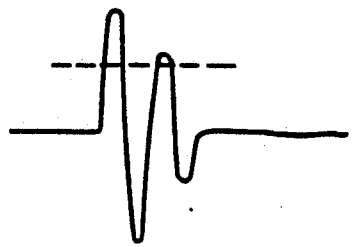

The wave-form of the electrical activity input to the input-output terminal 4 is shown in FIGS. 24 and 25(A). Further, the wave-form before the wave-form is differentiated and input to the amplification circuit 14 is shown in FIGS. 24 and 25(B). The wave-form shown in FIG. 25 is reverse in polarity from the wave-form shown in FIG. 24, so as mentioned above, it is not known which wave-form enters the input-output terminal 4 according to the mounting position of the catheter etc.

Figure 25C:
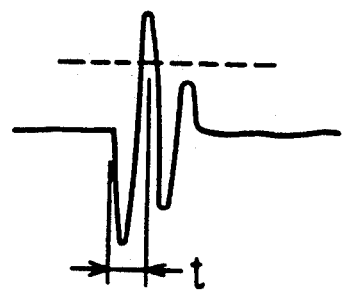

According to the embodiment, input signal from the filter circuit 51 is directly applied to comparison circuit 52a without the absolute value circuit 60 of the third pacemaker shown in FIG. 19. The wave-form of the R wave input to the comparison circuit 52a, as shown in FIGS. 24 and 25(C), inverts and changes in accordance with the state of the wave-form of the R wave input to the input-output terminal 4, but whatever the case if the R wave is input, a wave of a positive polarity more than the comparison level is input to the comparison circuit, so it is possible to detect an R wave. However, when an inverted wave-form such as shown in FIG. 25 is input to the comparison circuit 52a, a detection time lag "t" occurs compared with the case where the wave-form shown in FIG. 24 is input. The detection time lag "t" is about 30 to 50 milliseconds, so is no problem.

The other construction and the operation of the embodiment is same as the third pace maker shown in FIG. 19.

If this construction is adopted, even if a switch element is not used, there is no longer any erroneous detection of the pacing pulse and the after potential by the comparison circuit 52a as an R wave. Further, even if a switch element is used, the pulse due to the leakage current etc. does not have any effect on the detection of the R wave. The reason is that the switch operation is performed at the negative side opposite in polarity to the signal to be detected (no positive noise is produced).

Figure 26:
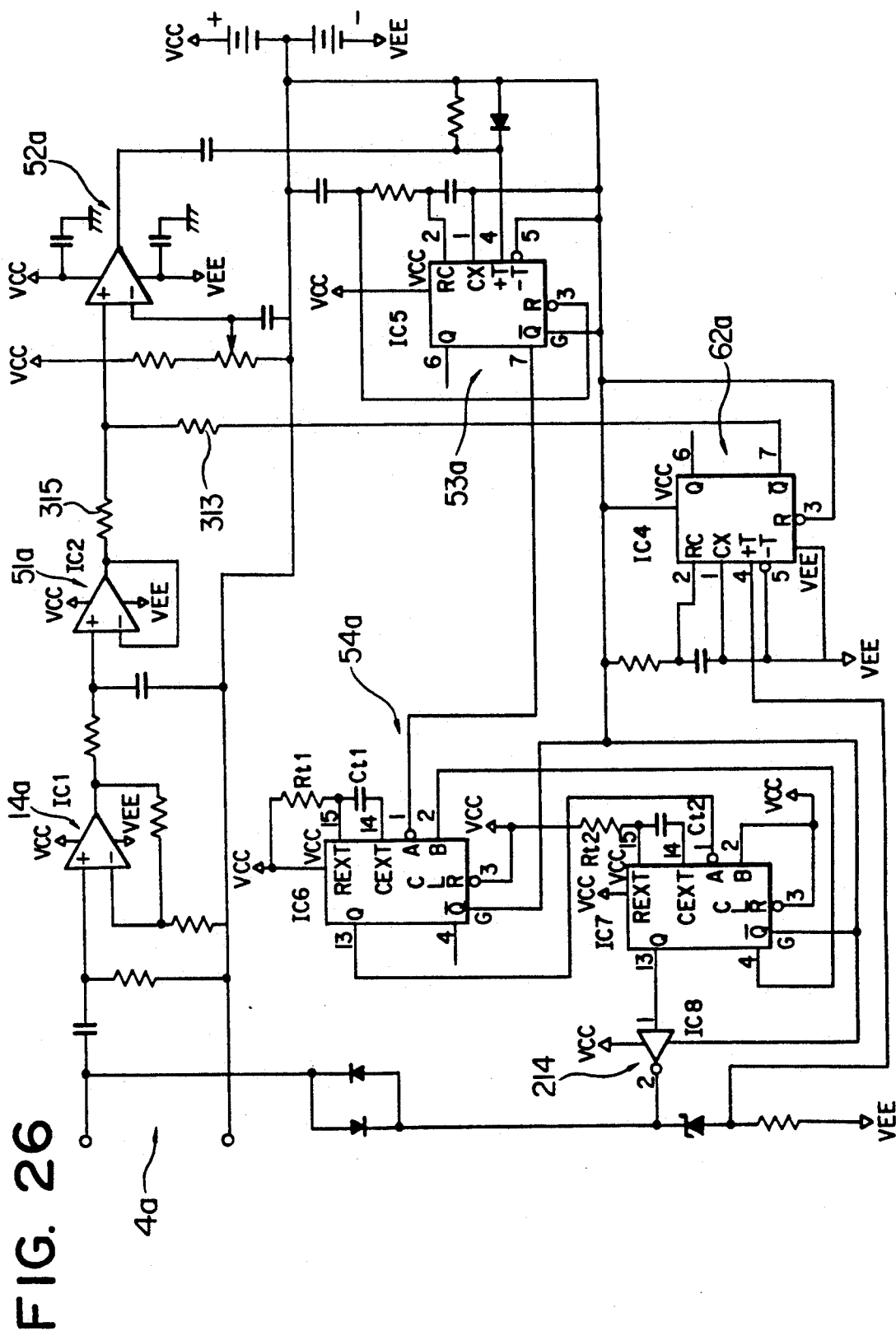
FIG. 26 is a circuit diagram in greater detail than the block diagram of FIG. 23.

A more detailed circuit diagram of the pacemaker shown in FIG. 23 is shown in FIG. 26.

In FIG. 26, the reference 4a is an input-output terminal, and 14a is an amplification circuit which is comprised of an operational amplifier and has an amplification rate of several 100. Reference 51a is a filter, which filter is, for example, comprised of the low pass type and has a buffer of an operational amplifier. Reference 52a is a comparison circuit, which is comprised of the operational amplifier performing a comparator operation and is designed that the comparison potential is finely adjusted to the positive side. In the comparison circuit 52a, when a potential higher than the comparison potential is input, an output signal of a positive polarity is output, while at other times, a negative output signal is produced. The output from the filter circuit 51a is connected to the input end of the comparison circuit 52a through a resistor 315.

Reference numeral 62a is a switch signal generator, which operates with a negative power source. The switch signal generator is comprised of a one-shot multi-vibrator which shifts the level of the pacing output to make it a negative level and which enables, in synchronization with the rise of the pacing output, an output from 0 to the negative side from the output "$\overline{Q}$" and an output from the negative side to 0 from the output "Q".

The one-shot multiviblator 62a is designed that the output starts to appear in synchronization with the rise of the pacing pulse and the output is stopped after tens to hundreds of milliseconds or so. The output side of the switch signal generator 62a is connected to the input side of the comparison circuit 52a through a resistor 313. The switch signal generator 62a and the resistors 313 and 315 comprise a pulse lowering circuit 62 as shown in FIG. 23.

Figure 27:
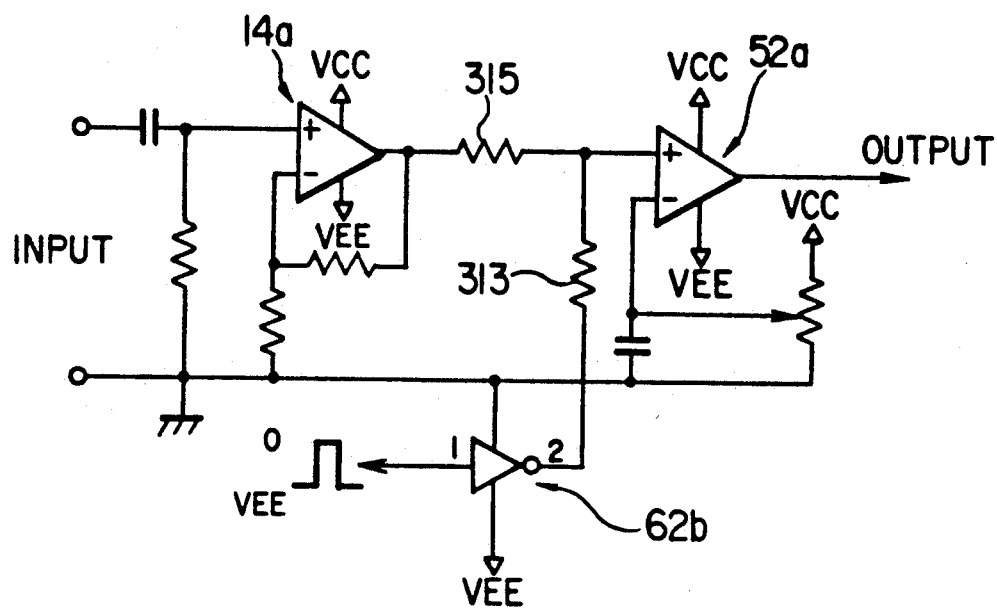
FIGS. 27, 28, 29, and 30 are circuit diagrams showing modifications of a pulse lowering circuit shown in FIG. 23.

A circuit diagram explaining in a simplified form the circuit around the comparison circuit 52a shown in FIG. 26 is shown in FIG. 27. In the circuit shown in FIG. 27, the output signal from the amplification circuit 14a is input directly to the comparison circuit 52a through the resistor 315. In the figure, the switch signal generator is shown by the reference 62b.

Figure 28:
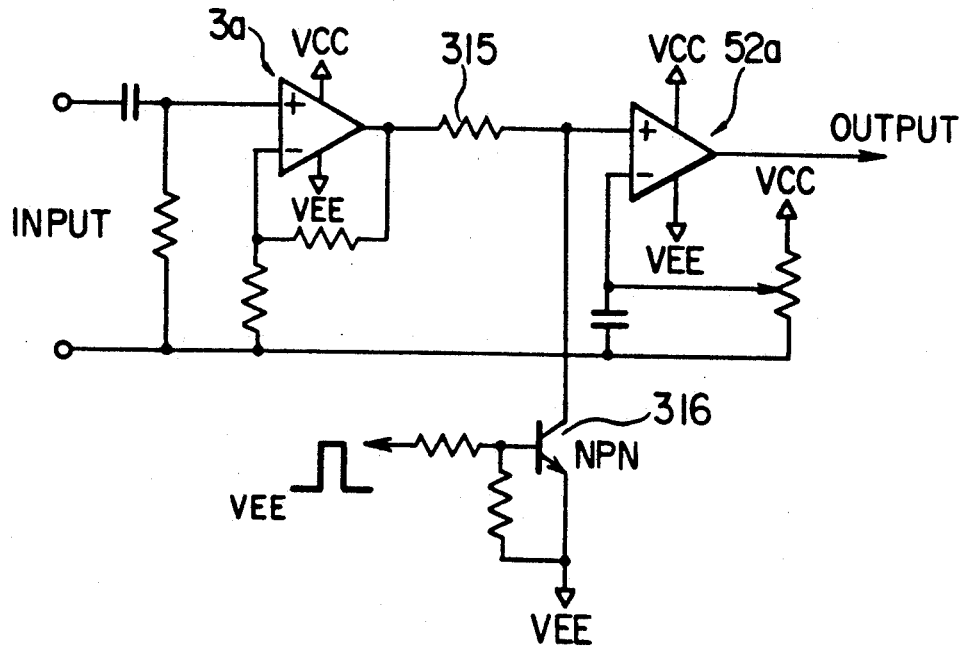

As another circuit example, as shown in FIG. 28, it is possible to connect an open collector or an open drain transistor 316 from the output of the signal generator 62a to the input end of the comparison circuit 52a, connect the emitter or the source to the negative power source, and switch the base or gate by the negative potential. Even with this circuit, it is possible to lower to a negative potential.

Figure 29:
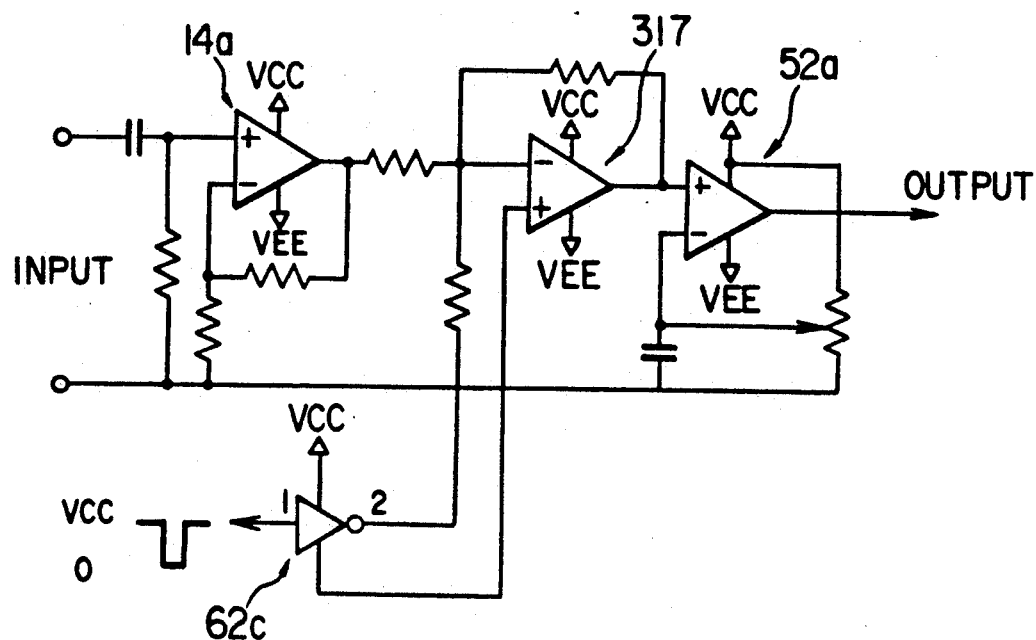
Figure 30:
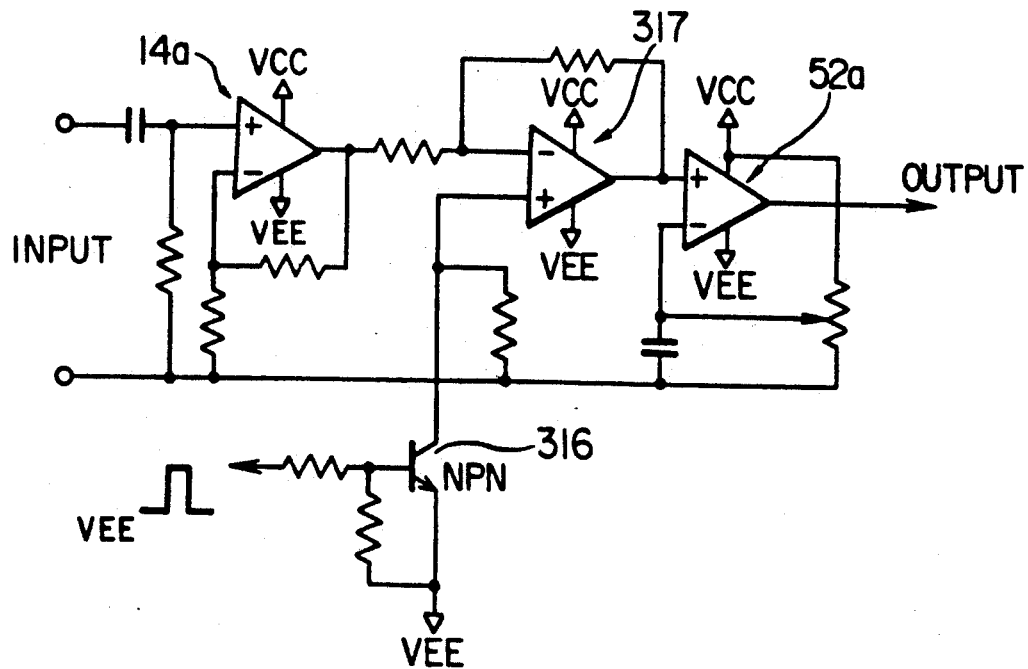
Figure 31:
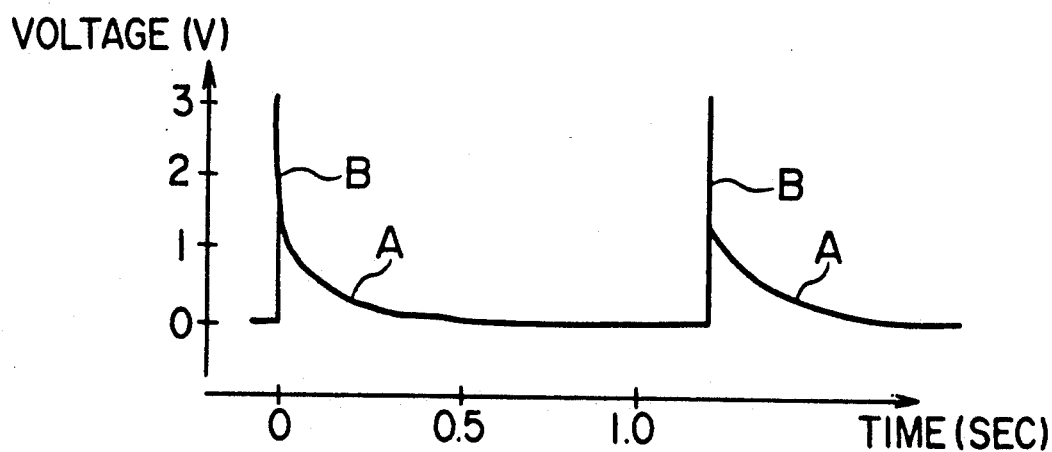
FIG. 31 is a graph showing the wave-form of a pacing pulse.

Alternatively, as shown in FIG. 29, an inverted amplification circuit 317 may be connected in the state of a DC coupling before the input of the comparison circuit 52a so that the input of the comparison circuit 52a is lowered to the negative side before the input end of the comparison circuit 52a. Thereby, it is possible at the input side of the inverted amplification circuit 317 to raise the signal to the positive side by a switch potential generation circuit which is the same as the above-mentioned circuit 62c except for having an opposite polarity. Further, as similarly shown in FIG. 30, if an inverted amplification circuit 317 is directly connected before the input of the comparison circuit 52a, the potential of the non-inverted terminal of the inverted amplification circuit 317 may be lowered to the negative side using a transistor 316 as shown in FIG. 28.

Further, even if the comparison potential sides of the comparison circuits 52, 52a are raised to the positive side, the same operation as above can be performed and, for the electronic circuit designer, this would be more proper and easier to conceive. However, normally the comparison potential terminal has a capacitor inserted to prevent fluctuations and noise, therefore when the potential is greatly changed, the speed slows down and, at the same time, insertion of a semiconductor device here would result in fluctuation of the comparison potential and fluctuation of the R wave detection sensitivity due to changes in temperature, so in general this is not preferable.

Above, an explanation was made considering the comparison polarity of the comparison circuit to be a positive polarity, but even if conversely the comparison potential is made negative and the signal is raised to the positive side by the switch signal, the same would apply.

On the other hand, the switch signal generators 62a, 62b may be one-shot multi-vibrators or microcomputers which start operating in synchronization with the rise of the pacing pulse and continue operating until the time where it is envisioned that the after potential then ends (usually, about 300 milliseconds, but shortened to 30 to 150 milliseconds by provision of an attenuation circuit). The output is left as is or is inverted or shifted in level etc. and the said switch signal generators are driven by potentials convenient for the same.

Reference numeral 53a in FIG. 26 is a one-shot multi-vibrator which stops the detection for approximately 250 to 300 milliseconds after detection of the electrical activity of the heart. This multi-vibrator 53a has the function of receiving the output signal of the comparison circuit 52a, sending the reset signal to the pacing pulse generation circuit 54a, and resetting so that the pacing pulse from the pacing pulse generation circuit 54a is not output to the input-output terminal 4. That is, the multi-vibrator 53a corresponds to the detection stopping circuit 153a and the pacing pulse reset circuit 153b shown in FIG. 23.

Note that the pacing pulse generation circuit 54a is comprised of two one-shot multi-vibrators and is designed to set the pulse interval and the pulse width by t1 and t2. Reference numeral 214 is a pacing pulse output stage.

The present invention is not limited to the above-mentioned embodiments and can be modified in various ways in the scope of the invention.

According to the fourth pacemaker of the present invention, it is possible to prevent the comparison circuit from detecting the pacing pulse and the following after potential without provision of a switching circuit to prevent detection of the pacing pulse. Further, even if use is made of a switching circuit, the pulse due to the leakage current etc. does not have an effect on the detection of the R wave.

Further, according to the circuit of the pacemaker of the present invention, a production efficiency of the pacemaker is improved.

An explanation will now be made of the present invention using more detailed examples, however, the present invention is not limited to these examples.

A circuit as shown in FIG. 26 was prepared.

As the amplification circuit 14a, use was made of an operational amplifier having a 201 fold amplification rate and comprised of an LM4250(IC1). As the filter circuit 51a, use was made of a low pass type having a buffer of an operational amplifier (IC2=LM4250). As the comparison circuit, use was made of an operational amplifier (IC5=LM4250) made to perform a comparator operation and finely adjusting the comparison potential to the positive side. As the switch signal generator 62a operating with a negative power source, use was made of a one-shot multi-vibrator (IC6=COMS4538) which shifts the level of the pacing output to make it a negative level and which enables, in synchronization with the rise of the pacing output, an output from 0 to the negative side from the output "$\overline{Q}$" and an output from the negative side to 0 from the output "Q". The one-shot multivibration 62a was designed that the output started to appear in synchronization with the rise of the pacing pulse and the output is stopped after approximately 60 milliseconds.

As the one-shot multi-vibrator 53a, use was made of one which detects the electrical activity of the heart and then stops the detection for 250 to 300 milliseconds. As the pacing pulse generation circuit 9a, use was made of one which is made to set the pulse interval and pulse width by t1 and t2.

To the input-output terminal of the circuit was connected a pseudo load circuit 2 as shown in FIG. 32. When this was operated, the pacing pulse and after potential were effectively eliminated and there was no noise of switching.

Many widely different embodiments of the present invention may be constructed without departing from the spirit and scope of the present invention, and it should be understood that the present invention is not restricted to the specific embodiments described above.

We claim:

1. A pacemaker comprising:
   electrodes disposed in a heart for detecting electrical activity of the heart;
   R wave detection means for detecting an R wave of the electrical activity of the heart input from said electrodes, said R wave detection means issuing an output signal when the R wave is detected;
   pacing pulse generation means for discriminating a cycle of the R wave based on the output signal of said R wave detection means, said pacing pulse generation means only outputting a pacing pulse from said electrodes after the R wave is not detected for more than a predetermined interval;
   input-output terminal means for transmitting the input signal from said electrodes to said R wave detection circuit and which transmits the output signal from said pacing pulse generation circuit toward said electrodes;
   output circuit means connected between said input-output terminal means and said pacing pulse generation means, said output circuit means for setting a high output impedance of more than 5 kilohms when the potential of the input signal transmitted through said input-output terminal means is within a predetermined range, and for setting a low output impedance when the potential of said signal is outside of said range, said output circuit means including voltage determining means for determining when the potential of the input signal is within a predetermined range, and for determining when the potential of the signal is outside of the range.

2. A pacemaker as set forth in claim 1, wherein said predetermined range is narrower than the range of −600 mV to +600 mV.

3. A pacemaker as set forth in claim 1, wherein said R wave detection means comprises comparison circuit means, for comparing an input signal input thereto to a predetermined value, said comparison circuit means generating an output signal when said input signal exceeds said predetermined value, thereby detecting the R wave of the electrical activity of the heart input from the electrodes.

4. A pacemaker as set forth in claim 1, wherein said output circuit means is an emitter-follower complementary push-pull circuit, and emitter terminals of two transistors forming the push-pull circuit are connected to said input-output terminal means, said output circuit means including biasing means for biasing the transistors, wherein the two transistors have biases of 20 to 600 mV lower than the bias values between the bases and emitters of the transistors.

5. A pacemaker as set forth in claim 4, wherein said biasing means comprises diodes connected between the bases of the two transistors, said biases being determined by a forward direction falling voltage of said diodes.

6. A pacemaker as set forth in claim 4, wherein said biasing means comprises a constant current circuit.

7. A pacemaker as set forth in claim 1, wherein said R wave detection means comprises comparison circuit means, for comparing an input signal input thereto to a predetermined value, said comparison circuit means generating an output signal when said input signal exceeds said predetermined value, thereby detecting the R wave of the electrical activity of the heart input from the electrodes.

8. A pacemaker as set forth in claim 7, said pacemaker further comprising:
absolute value circuit means placed at the input side of said comparison circuit means, said absolute value circuit means shifting the input signal entering said comparison circuit means to a signal of one of a positive and negative unipolarity; and
pulse lowering circuit means for adding to the input signal of the unipolarity entering said comparison circuit means from the absolute value circuit means a lowering pulse of a polarity opposite to that polarity and of a potential larger than the input signal for a predetermined period.

9. A pacemaker comprising:
electrodes disposed in a heart for detecting electrical activity of the heart;
R wave detection means for detecting an R wave of the electrical activity of the heart input from the electrodes, said R wave detection means issuing an output signal when the R wave is detected;
pacing pulse generation means for discriminating a cycle of the R wave based on the output signal of said R wave detection means, said pacing pulse generation means only outputting a pacing pulse from said electrodes after the R wave is not detected for more than a predetermined interval;
input-output terminal means for transmitting the input signal from said electrodes to said R wave detection circuit and which transmits the output signal from said pacing pulse generation means toward said electrodes;
output circuit means for actively outputting one voltage of substantially 0 V and substantially the same voltage as the power source voltage, said output circuit means being disposed between said pacing pulse generation circuit means and said input-output terminal means; and
a pair of diodes connected in parallel and reverse to each other, said diodes being disposed between said pacing output circuit means and said input-output terminal means, said diodes for determining the voltage output from said output circuit means.

10. A pacemaker as set forth in claim 9, wherein said output circuit means outputs one of a minimum output voltage of 0 plus or minus 0.6 V and a maximum output voltage of the power source voltage minus 0.6 V or more, and
said pair of diodes are silicon Schottky barrier diodes.

11. A pacemaker as set forth in claim 9, wherein said pair of diodes are silicon Schottky barrier diodes.

12. A pacemaker as set forth in claim 9, wherein said R wave detection means comprises comparison circuit means, for comparing an input signal input thereto to a predetermined value, said comparison circuit means generating an output signal when said input signal exceeds said predetermined value, thereby detecting the R wave of the electrical activity of the heart input from said electrodes.

13. A pacemaker as set forth in claim 9, further comprising:
absolute value circuit means placed at the input side of said comparison circuit means, said absolute value circuit means shifting the input signal entering said comparison circuit means to a signal of one of a positive and negative unipolarity; and
pulse lowering circuit means for adding to the input signal of the unipolarity entering the comparison circuit means from said absolute value circuit means a lowering pulse of a polarity opposite to that polarity and of a potential larger than the input signal for a predetermined period.

14. A pacemaker comprising:
electrodes disposed in a heart for detecting electrical activity of the heart;
comparison circuit means for comparing an input signal input thereto to a predetermined value, said comparison circuit means generating an output signal when said input signal exceeds said predetermined value, thereby detecting an R wave of the electrical activity of the heart input from said electrodes;
pacing pulse generation means for discriminating a cycle of the R wave based on the output signal of the comparison circuit means, said pacing pulse generation means only outputting a pacing pulse from said electrodes after the R wave is not detected for more than a predetermined interval;
absolute value circuit means placed at the input side of said comparison circuit means, said absolute value circuit means for shifting the input signal entering said comparison circuit means to a signal of one of a positive and negative unipolarity; and
pulse lowering circuit means for adding to the input signal of the unipolarity entering said comparison circuit means from said absolute value circuit means a lowering pulse of a polarity opposite to that polarity and of a potential larger than the input signal, said lowering pulse being added to the input signal for a predetermined period.

15. A pacemaker comprising:
electrodes disposed in a heart for detecting electrical activity of the heart;
comparison circuit means for comparing an input signal input thereto to a predetermined value, said comparison circuit means generating an output signal when said input signal exceeds said predetermined value, thereby detecting an R wave of the electrical activity of the heart input from said electrodes;
pacing pulse generation means for discriminating a cycle of the R wave based on the output signal of the comparison circuit means, said pacing pulse generation means only outputting a pacing pulse from said electrodes after the R wave is not detected for more than a predetermined interval; and
pulse lowering circuit means for adding to the input signal entering said comparison circuit means a lowering pulse of a polarity opposite to the input signal and of a potential larger than the input signal, said lowering pulse being added to the input signal for a predetermined period.

16. A pacemaker comprising:
electrodes disposed in a heart for detecting electrical activity of the heart;
R wave detection means for detecting an R wave of the electrical activity of the heart input from said electrodes, said R wave detection means issuing an output signal when the R wave is detected;
pacing pulse generation means for discriminating a cycle of the R wave based on the output signal of said R wave detection means, said pacing pulse generation means only outputting a pacing pulse from said electrodes after the R wave is not detected for more than a predetermined interval;

input-output terminal means for transmitting the input signal from said electrodes to said R wave detection circuit and which transmits the output signal from said pacing pulse generation circuit toward said electrodes;

output circuit means connected between said input-output terminal means and said pacing pulse generation means, said output circuit means for setting a high output impedance of more than 5 kilohms when the potential of the input signal transmitted through said input-output terminal means is within a predetermined range, and for setting a low output impedance when the potential of said signal is outside of said range, said output circuit means comprising an emitter-follower complementary push-pull circuit, wherein emitter terminals of two transistors forming the push-pull circuit are connected to said input-output terminal means, said output circuit means including biasing means for biasing the transistors, wherein the two transistors have biases of 20 to 600 mV lower than the bias values between the bases and emitters of the transistors, said output circuit means also including voltage determining means for determining when the potential of the input signal is within a predetermined range, and for determining when the potential of the signal is outside of the range.

17. A pacemaker as set forth in claim 16, wherein said predetermined range is narrower than the range of −600 mV to +600 mV.

* * * * *